United States Patent
Walter

(10) Patent No.: US 11,903,706 B2
(45) Date of Patent: *Feb. 20, 2024

(54) DETECTING AN ANALYTE IN A BODY FLUID

(71) Applicant: Roche Diabetes Care, Inc., Indianapolis, IN (US)

(72) Inventor: Helmut Walter, Heppenheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,237

(22) Filed: Aug. 2, 2023

(65) Prior Publication Data

US 2023/0371857 A1 Nov. 23, 2023

Related U.S. Application Data

(63) Continuation of application No. 16/069,016, filed as application No. PCT/EP2017/052360 on Feb. 3, 2017, now Pat. No. 11,759,132.

(30) Foreign Application Priority Data

Feb. 5, 2016 (EP) .................................... 16154468

(51) Int. Cl.
*A61B 5/1473* (2006.01)
*A61B 5/00* (2006.01)
(Continued)

(52) U.S. Cl.
CPC ........ *A61B 5/1473* (2013.01); *A61B 5/14503* (2013.01); *A61B 5/14532* (2013.01);
(Continued)

(58) Field of Classification Search
CPC .............. A61B 5/1473; A61B 5/14503; A61B 5/14532; A61B 5/14546; A61B 5/14865;
(Continued)

(56) References Cited

U.S. PATENT DOCUMENTS

| 5,413,690 A | 5/1995 | Kost et al. |
| 5,762,770 A | 6/1998 | Pritchard et al. |

(Continued)

FOREIGN PATENT DOCUMENTS

| CN | 1703254 | 11/2005 |
| CN | 101596104 | 12/2009 |

(Continued)

OTHER PUBLICATIONS

Office Action in U.S. Appl. No. 16/068,743 dated Apr. 1, 2022.
(Continued)

*Primary Examiner* — Patrick Fernandes
*Assistant Examiner* — Joseph A Tombers
(74) *Attorney, Agent, or Firm* — Woodard, Emhardt, Henry, Reeves & Wagner, LLP

(57) ABSTRACT

A medical device for detecting at least one analyte in a body fluid is disclosed. The medical device comprises:
at least one analyte sensor having an insertable portion adapted for at least partially being inserted into a body tissue of a user,
at least one insertion cannula, wherein the analyte sensor at least partially is placed inside the insertion cannula;
at least one housing, wherein the housing comprises at least one sensor compartment, wherein the sensor compartment forms a sealed compartment receiving at least the insertable portion of the analyte sensor, wherein the sealed compartment comprises at least one detachable upper cap and at least one detachable lower cap, wherein the detachable lower cap is configured for (Continued)

detachment before insertion, thereby opening the insertable portion for insertion, wherein the insertion cannula is attached to the detachable upper cap, wherein the detachable upper cap is configured for detachment after insertion, thereby removing the insertion cannula; and at least one electronics unit, wherein the analyte sensor is operably connected to the electronics unit, wherein the electronics unit comprises at least one interconnect device with at least one electronic component attached thereto, wherein the interconnect device fully or partially surrounds the housing.

27 Claims, 5 Drawing Sheets

(51) Int. Cl.
*A61B 5/145* (2006.01)
*A61B 5/1486* (2006.01)
*B08B 5/00* (2006.01)
*B08B 7/00* (2006.01)

(52) U.S. Cl.
CPC ...... *A61B 5/14546* (2013.01); *A61B 5/14865* (2013.01); *A61B 5/6849* (2013.01); *B08B 5/00* (2013.01); *B08B 7/0035* (2013.01); *A61B 5/688* (2013.01); *A61B 2560/063* (2013.01); *A61B 2562/166* (2013.01); *A61B 2562/242* (2013.01)

(58) Field of Classification Search
CPC . A61B 5/6849; A61B 5/688; A61B 2560/063; A61B 2562/166; A61B 2562/242; B08B 5/00; B08B 7/0035
See application file for complete search history.

(56) References Cited

U.S. PATENT DOCUMENTS

| | | | |
|---|---|---|---|
| 5,798,031 | A | 8/1998 | Charlton et al. |
| 6,129,823 | A | 10/2000 | Hughes et al. |
| 6,256,523 | B1 | 7/2001 | Diab et al. |
| 6,360,888 | B1 | 3/2002 | McIvor et al. |
| 8,577,437 | B2 | 11/2013 | Roesicke et al. |
| 8,721,544 | B2 | 5/2014 | Roesicke et al. |
| 8,764,657 | B2 | 7/2014 | Curry et al. |
| 9,164,056 | B2 | 10/2015 | Harrison et al. |
| 9,693,713 | B2 | 7/2017 | Pace et al. |
| 2005/0012731 | A1 | 1/2005 | Yamazaki et al. |
| 2005/0013731 | A1 | 1/2005 | Burke et al. |
| 2005/0101912 | A1 | 5/2005 | Faust et al. |
| 2005/0158205 | A1 | 7/2005 | Swanson et al. |
| 2005/0283114 | A1 | 12/2005 | Bresina et al. |
| 2006/0020186 | A1 | 1/2006 | Brister et al. |
| 2007/0073129 | A1 | 3/2007 | Shah et al. |
| 2007/0189928 | A1 | 8/2007 | Sabol |
| 2007/0202488 | A1 | 8/2007 | Hendrix et al. |
| 2008/0027296 | A1 | 1/2008 | Hadvary et al. |
| 2008/0097246 | A1 | 4/2008 | Stafford |
| 2008/0190766 | A1 | 8/2008 | Rush et al. |
| 2008/0234561 | A1 | 9/2008 | Roesicke et al. |
| 2008/0242962 | A1 | 10/2008 | Roesicke et al. |
| 2008/0255440 | A1 | 10/2008 | Eilersen et al. |
| 2008/0319278 | A1 | 12/2008 | Omtveit et al. |
| 2009/0105569 | A1 | 4/2009 | Stafford |
| 2010/0049014 | A1 | 2/2010 | Funderburk et al. |
| 2010/0200538 | A1 | 8/2010 | Petisce et al. |
| 2010/0286714 | A1 | 11/2010 | Gyrn et al. |
| 2010/0324392 | A1 | 12/2010 | Yee et al. |
| 2010/0331738 | A1 | 12/2010 | Stein et al. |
| 2011/0288574 | A1 | 11/2011 | Curry et al. |
| 2012/0053608 | A1 | 3/2012 | Shoshihara et al. |
| 2012/0083673 | A1 | 4/2012 | Al-Ali et al. |
| 2012/0116190 | A1 | 5/2012 | Iketani et al. |
| 2012/0190952 | A1 | 7/2012 | Stafford |
| 2012/0197222 | A1 | 8/2012 | Donnay et al. |
| 2012/0215083 | A1 | 8/2012 | Shoshihara et al. |
| 2012/0259192 | A1 | 10/2012 | Tsukada et al. |
| 2013/0018454 | A1 | 1/2013 | Lelkes et al. |
| 2013/0150691 | A1 | 6/2013 | Pace et al. |
| 2013/0267813 | A1 | 10/2013 | Pryor et al. |
| 2013/0313130 | A1 | 11/2013 | Little et al. |
| 2014/0066730 | A1 | 3/2014 | Roesicke et al. |
| 2015/0018643 | A1 | 1/2015 | Cole et al. |
| 2015/0080684 | A1 | 3/2015 | Frey et al. |
| 2016/0022179 | A1 | 1/2016 | Di Resta et al. |
| 2016/0058471 | A1 | 3/2016 | Peterson et al. |
| 2016/0287150 | A1 | 10/2016 | Yu |
| 2016/0331284 | A1 | 11/2016 | Pace |
| 2017/0202488 | A1 | 7/2017 | Stafford |
| 2017/0202497 | A1 | 7/2017 | Yee et al. |
| 2017/0251922 | A1 | 9/2017 | Roesicke et al. |
| 2018/0325433 | A1 | 11/2018 | Prais et al. |
| 2018/0360358 | A1 | 12/2018 | Baker et al. |
| 2018/0360493 | A1 | 12/2018 | Baker et al. |
| 2019/0151564 | A1 | 5/2019 | Schrul et al. |
| 2019/0231238 | A1 | 8/2019 | Frey et al. |

FOREIGN PATENT DOCUMENTS

| | | |
|---|---|---|
| CN | 102245236 | 11/2011 |
| CN | 102387746 | 3/2012 |
| CN | 102469967 | 5/2012 |
| CN | 102525413 | 7/2012 |
| CN | 103156619 | 6/2013 |
| CN | 104394757 | 3/2015 |
| CN | 104470422 | 3/2015 |
| CN | 204233136 | 4/2015 |
| CN | 204233137 | 4/2015 |
| CN | 104780835 | 7/2015 |
| CN | 105534508 | 5/2016 |
| DE | 954712 | 12/1956 |
| DE | 20020566 | 1/2002 |
| EP | 1475113 | 11/2004 |
| EP | 1929941 | 6/2008 |
| EP | 1972269 | 9/2008 |
| EP | 2163190 | 3/2010 |
| EP | 2919000 | 9/2015 |
| EP | 2982303 | 2/2016 |
| EP | 14180045.8 | 2/2016 |
| EP | 3202323 | 8/2017 |
| JP | 2004049607 | 2/2004 |
| JP | 2004229674 | 8/2004 |
| JP | 2008522786 | 7/2008 |
| JP | 2009525794 | 7/2009 |
| JP | 2012071109 | 4/2012 |
| JP | 2013523216 | 6/2013 |
| JP | 2014144025 | 8/2014 |
| JP | 2015515305 | 5/2015 |
| KR | 101393856 | 8/2012 |
| RU | 133942 U1 | 10/2013 |
| WO | WO 2006/015922 | 2/2006 |
| WO | WO 2010/091005 | 8/2010 |
| WO | WO 2010/091028 | 8/2010 |
| WO | WO 2011/119896 | 9/2011 |
| WO | WO 2011/121023 | 10/2011 |
| WO | WO 2011/037030 | 2/2013 |
| WO | WO 2013/090215 | 6/2013 |
| WO | WO 2013/144255 | 10/2013 |
| WO | WO 2014/018928 A1 | 1/2014 |
| WO | WO 2014/179343 | 11/2014 |
| WO | WO 2016/012482 | 1/2016 |
| WO | WO 2016/012497 | 1/2016 |
| WO | WO 2016/036924 | 3/2016 |
| WO | WO 2017/019224 | 2/2017 |
| WO | WO 2017/037191 | 3/2017 |
| WO | WO 2017/116915 | 7/2017 |
| WO | WO 2018/195286 | 10/2018 |

(56) References Cited

FOREIGN PATENT DOCUMENTS

| WO | WO 2018/215421 | 11/2018 |
| WO | WO 2018/222010 | 12/2018 |

OTHER PUBLICATIONS

Office Action in U.S. Appl. No. 16/068,743 dated Dec. 22, 2020.
Office Action in U.S. Appl. No. 16/068,743 dated May 24, 2021.
Office Action in U.S. Appl. No. 16/068,743 dated Sep. 23, 2021.
Office Action in U.S. Appl. No. 16/898,049 dated May 10, 2022.
Response to Office Action in U.S. Appl. No. 16/068,743 dated Aug. 24, 2021.
Response to Office Action in U.S. Appl. No. 16/068,743 dated Dec. 15, 2021.
Response to Office Action in U.S. Appl. No. 16/068,743 dated Jul. 28, 2022.
Response to Office Action in U.S. Appl. No. 16/068,743 dated Mar. 22, 2021.
Office Action in U.S. Appl. No. 18/228,283 dated Sep. 26, 2023.
Office Action in U.S. Appl. No. 18/228,754 dated Sep. 27, 2023.

DETECTING AN ANALYTE IN A BODY FLUID

FIELD OF THE INVENTION

The invention relates to a medical device for detecting at least one analyte in a body fluid, a method for assembling a medical device and a method of using a medical device. The device and methods according to the present invention may mainly be used for long-term monitoring of an analyte concertation in a body fluid, such as for long-term monitoring of a blood glucose level or of the concentration of one or more other types of analytes in a body fluid. The invention may both be applied in the field of home care as well as in the field of professional care, such as in hospitals. Other applications are feasible.

RELATED ART

Monitoring certain body functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown e.g. in DE 954712 B. Other techniques for providing electrical contacts, such as by appropriate spring contacts, are generally known and may be applied.

In order to avoid detrimental effects of the aggressive environment onto the conductive properties of the electrical contact, the region of the electrical contact is typically encapsulated and protected against humidity. Generally, encapsulations of electrical locks and contacts by using appropriate seals is known from e.g. DE 200 20 566 U1. Specifically in transcutaneous or subcutaneous sensors, in which the region of electrical contact between the sensor and the control part is close to the human skin, an efficient protection against humidity, dirt, sweat and detergents, such as detergents used for body care, is crucial.

US2012/0197222 A1 discloses medical device inserters and processes of inserting and using medical devices. A method is disclosed which comprises removing a substantially cylindrical cap from an inserter to expose a substantially cylindrical sleeve; removing a cover from a substantially cylindrical container holding sensor components; and fitting the sensor components into the inserter.

WO 2010/091028 A1 discloses an integrated analyte monitoring device assembly. The integrated analyte monitoring device assembly comprises an analyte sensor for transcutaneous positioning through a skin layer and maintained in fluid contact with an interstitial fluid under the skin layer during a predetermined time period. The analyte sensor has a proximal portion and a distal portion. Sensor electronics are coupled to the analyte sensor. The sensor electronics comprises a circuit board having a conductive layer and a sensor antenna disposed on the conductive layer. Further, the sensor electronics comprises one or more electrical contacts provided on the circuit board and coupled with the proximal portion of the analyte sensor to maintain continuous electrical communication. Further, the sensor electronics comprises: a data processing component provided on the circuit board and in signal communication with the analyte sensor. The data processing component is configured to execute one or more routines for processing signals received from the analyte sensor. Further, the data processing component is configured to control the transmission of data associated with the processed signals received from the analyte sensor to a remote location using the sensor antenna in response to a request signal received from the remote location.

WO 2014/018928 A1 discloses on-body analyte monitoring devices configured for uncompressed and compressed configurations and methods of using the analyte monitoring devices. The devices comprise a collapsible housing, wherein upon desired placement and user application of force to the housing converts the analyte monitoring device from an uncompressed configuration to a low-profile compressed state while guiding an analyte sensor through the skin and into contact with bodily fluid to measure an analyte level therein. Also provided are systems and kits.

European patent application number 14 180 045.8, filed on Aug. 6, 2014, discloses a medical device and a method for producing a medical device. The medical device comprises at least one implantable device having at least one implantable portion adapted for at least partially being implanted into a body tissue of a user. The implantable device further has at least one contact portion connected to the implantable portion. The medical device further comprises at least one housing. The housing is configured to receive the implantable portion. The housing is configured to provide a sterile packaging such that the implantable portion is sealed against a surrounding environment. The housing comprises at least one first part and at least one second part. The first part and the second part are removable connectable to form the sterile packaging. The first part comprises at least one first sealing surface and the second part comprises at least one second sealing surface. The first sealing surface and the second sealing surface interact to form a sealing area. The implantable device has an interconnecting portion connecting the implantable portion and the contact portion. The interconnecting portion is led through the sealing area.

Despite the advantages and the progress achieved by the above-mentioned developments, specifically in the field of continuous monitoring technology, some significant technical challenges remain. Thus, generally, known techniques for protecting an electrical contact between a sensor and a control part generally are rather complex. An assembly of a plurality of components is generally required, which typically implies a complex and costly manufacturing process. Further, known techniques generally require voluminous components, which is an issue, specifically considering the fact that miniaturizing the sensor systems is a factor contributing to the convenience of use. Specifically in case complex encapsulation parts manufactured by plastic molding techniques are required for protecting the electrical contacts, a rising of costs and sensor volume typically has to be taken into account. Further, cleaning of complex protective covers, such as protections including O-rings or other seals, turns out to be difficult.

Problem to be Solved

It is therefore an objective of the present invention to provide a medical device for detecting at least one analyte in a body fluid, a method for assembling a medical device and a method of using a medical device, which at least partially avoid the shortcomings of known devices and methods of this kind and which at least partially address the above-mentioned challenges. Specifically, a device and methods shall be disclosed which allow for easy manufacturing and simple handling processes by a user.

SUMMARY OF THE INVENTION

This problem is solved by a medical device for detecting at least one analyte in a body fluid, a method for assembling a medical device and a method of using a medical device, having the features of the independent claims. Preferred embodiments of the invention, which may be realized in an isolated way or in any arbitrary combination, are disclosed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a medical device for detecting at least one analyte in a body fluid is disclosed. The medical device comprises at least one analyte sensor having an insertable portion adapted for at least partially being inserted into a body tissue of a user. The medical device further comprises at least one insertion cannula. The analyte sensor is at least partially placed inside the insertion cannula. Further, the medical device comprises at least one housing. The housing comprises at least one sensor compartment configured to at least partially receive the analyte sensor. The sensor compartment forms a sealed compartment receiving at least the insertable portion of the analyte sensor. The sealed compartment comprises at least one detachable upper cap and at least one detachable lower cap. The detachable lower cap is configured for detachment before insertion, thereby opening the insertable portion for insertion. The insertion cannula is attached to the detachable upper cap. The detachable upper cap is configured for detachment after insertion, thereby removing the insertion cannula. Further, the medical device comprises at least one electronics unit. The analyte sensor is operably connected to the electronics unit. The electronics unit comprises at least one interconnect device with at least one electronic component attached thereto. The interconnect device fully or partially. i.e. at least partially, surrounds the housing.

As generally used within the present invention, the term "medical device" may refer to an arbitrary device configured for conducting at least one medical analysis and/or at least one medical procedure. The medical device therefore generally may be an arbitrary device configured for performing at least one diagnostic purpose and/or at least one therapeutic purpose. In the following, without restricting further embodiments, the present invention mainly will be described in terms of a medical device configured for performing at least one diagnostic purpose and, specifically, a medical device comprising at least one analyte sensor for performing at least one analysis. The medical device specifically may comprise an assembly of two or more components capable of interacting with each other, such as in order to perform one or more diagnostic and/or therapeutic purposes, such as in order to perform the medical analysis and/or the medical procedure. Specifically, the two or more components may be capable of performing at least one detection of the at least one analyte in the body fluid and/or in order to contribute to the at least one detection of the at least one analyte in the body fluid. The medical device generally may also be or may comprise at least one of a sensor assembly, a sensor system, a sensor kit or a sensor device.

The medical device may be a disposable medical device. The term "disposable medical device" may generally refer to an arbitrary medical device configured to be disposed of after use. Thus, one or more materials may specifically be low priced and/or easily recyclable. Specifically, the electronics unit may be a single-use electronics unit. The term "single-use" may generally refer to a property of an arbitrary element of being configured to be applied only for one time. Thus, after detecting the at least one analyte in the body fluid, the user may remove the electronics units from the body tissue, dispose the electronics unit and may utilize a further, new medical device comprising a further, new electronics unit for another detection of the analyte in the body fluid.

As generally used within the present invention, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

As further used herein, the term "body fluid" generally may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may be an analyte-specific detection.

As further used herein, the term "detect" generally refers to the process of determining the presence and/or the quantity and/or the concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal. As further used herein, the term "determining a concentration" generally may refer to a process of generating at least one representative result or a plurality of representative results indicating the concentration of the analyte in the body fluid.

As further used herein, the term "analyte sensor" may generally refer to an arbitrary element which is adapted to perform the above-mentioned process of the detection and/or which is adapted to be used in the above-mentioned process of the detection. Thus, the sensor specifically may be adapted to determine the concentration of the analyte and/or a presence of the analyte.

The analyte sensor specifically may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The detection may be analyte-specific. The measurement may be a qualitative and/or a quantitative measurement. Still, other embodiments are feasible.

The analyte sensor may particularly be a transcutaneous sensor. As used herein, the term "transcutaneous sensor" generally refers to an arbitrary sensor which is adapted to be fully or at least partly arranged within the body tissue of the patient or the user. For this purpose, the analyte sensor comprises the insertable portion. The term "insertable portion" may generally refer to a part or component of an element configured to be insertable into an arbitrary body tissue. In order to further render the analyte sensor to be usable as a transcutaneous sensor, the analyte sensor may fully or partially provide a biocompatible surface, i.e. a surface which, at least during durations of use, do not have any detrimental effects on the user, the patient or the body tissue. Specifically, the insertable portion of the analyte sensor may have a biocompatible surface. As an example, the transcutaneous sensor, specifically the insertable portion, may fully or partially be covered with at least one biocompatible membrane, such as at least one polymer membrane or gel membrane which is permeable for the at least one analyte and/or the at least one body fluid and which, on the other hand, retains sensor substances such as one or more test chemicals within the sensor and prevents a migration of these substances into the body tissue. Other parts or components of the analyte sensor may stay outside of the body tissue. The other parts may be connectable to an evaluation device such as to the electronics units as will further be described below.

The transcutaneous sensor generally may be dimensioned such that a transcutaneous insertion is feasible, such as by providing a width in a direction perpendicular to an insertion direction of no more than 5 mm, preferably of no more than 2 mm, more preferably of no more than 1.5 mm. The sensor may have a length of less than 50 mm, such as a length of 30 mm or less, e.g. a length of 5 mm to 30 mm. As used herein, the term "length" may refer to a direction parallel to the insertion direction. It shall be noted, however, that other dimensions are feasible.

The term "insertion cannula" may generally refer to an arbitrary element which may be insertable into the body tissue of the user, particularly in order to deliver or to transfer a further element. Therefore, the insertion cannula may specifically be or may comprise a hollow tube or a hollow needle. The insertion cannula e.g. may comprise at least one cross-section selected from the group consisting of: round, elliptical, U-shaped, V-shaped. Still, other embodiments are feasible. Specifically, the insertion cannula may be a slotted cannula. The insertion cannula may be configured to be inserted vertically or at an angle of 90° to 30° to the body tissue of the user.

The medical device may further comprise at least one septum received in the sensor compartment. As generally used herein, the term "septum" may generally refer to an arbitrary sealing element configured for sealing of a volume or room providing an environmental protection against moisture and/or an ambient atmosphere, or the like. As an example, the septum may be or may comprise at least one pierceable foil, disk, shim, plug or plate, made of a material which may be pierced by the insertion cannula and which may re-seal a piercing hole generated by the insertion cannula after retraction of the insertion cannula. Specifically, the septum may be made of an elastic material such as an elastomer. The septum may be manufactured by injection molding, specifically by two-component injection molding. The septum may be penetrable by an elongate object with a small diameter such as by the insertion cannula. After a penetration by the elongate object, an opening of the septum caused by the elongate object may be closed itself and the septum may further be configured to provide a tight sealing from the environment of the volume or the room. Specifically, the septum may be configured for sealing a remainder of the sensor compartment after detachment of the detachable upper cap. The insertion cannula may be configured for being pulled through the septum when the detachable upper cap is detached from the housing.

Further, the insertion cannula may comprise at least one barbed hook configured to prevent a further movement of the insertion cannula after usage. As further used herein, the term "barbed hook" may refer to an arbitrary tool which may comprise a portion which is curved or indented such that the portion may be applied to hold another object. Moreover, the barbed hook may be shaped in a specific manner such that a passing of the other object through the barbed hook may only be possible in one direction, wherein, in the counter direction, a movement may be completely suppressed or at least to a large extent reduced. Specifically, this property may be realized by small, further hooks being located such that ends of the hooks may point in a direction opposing a direction in which the other object is movable.

The medical device may further comprise at least one retraction mechanism for retracting the insertion cannula after insertion of the insertable portion of the analyte sensor into the body tissue.

The term "retraction mechanism" may generally refer to an arbitrary construction which is configured to move an object in an opposite direction of a direction in which the object may have been moved before the retraction mechanism is applied. Therefore, the retraction mechanism may comprise at least one retraction spring element, more preferably at least one retraction spring element disposed between the housing and the insertion cannula and biased in order to retract the insertion cannula from the body tissue. The retraction mechanism may at least partially be comprised within the detachable upper cap.

As used herein, the term "electronics unit" generally refers to an arbitrary device having at least one electronic component. Specifically, the electronics unit may comprise at least one electronic component for one or more of performing a measurement with the analyte sensor, performing a voltage measurement, performing a current measurement, recording sensor signals, storing measurement signals or measurement data, transmitting sensor signals or measurement data to another device. The electronics unit may specifically be embodied as a transmitter or may comprise a transmitter, for transmitting data. Other embodiments of the electronic components are feasible.

The electronics unit comprises at least one interconnect device, preferably a printed circuit board, more preferably a flexible printed circuit board. As used herein, an interconnect device generally refers to an element or a combination of elements which are capable of carrying one or more electronics components and interconnecting these one or more electronics components, such as interconnecting the one or more electronics components electrically or electronically with each other and/or with one or more contact pads. As an example, the interconnect device may comprise a base and one or more electrical traces and/or one or more electrical contact pads disposed thereon and/or therein. As an example, the interconnect device may comprise a printed circuit board which may either be rigid or fully or partially be embodied as a flexible printed circuit board. The base, as an example, may be a flat element having a lateral extension which exceeds its width by at least a factor of 10, more preferably by at least a factor of 100 or even a factor of 1000. Other embodiments are feasible. Rigid materials which may be used for the base are fiber-enforced plastic materials such as fiber-enforced epoxy materials like glass-fiber-enforced epoxy materials such as FR-4. Other materials may be used. Specifically, as outlined above, the base may be a flexible base, such that the interconnecting device may fully or partially be embodied as a flexible printed circuit board. In this case, as an example, the flexible base may fully or partially be made of one or more flexible plastic materials such as one or more plastic foils or laminate, such as polyimides.

As outlined above, the electronics unit comprises at least one electronic component attached to the interconnect device. Therein, the at least one electronic component may directly or indirectly be attached to the interconnect device. As an example, the electronic component may directly be attached to the interconnect device by using one or more of soldering, bonding or electrically conductive adhesive. Thus, the interconnect device may comprise one or more contact pads, wherein corresponding contacts of the electronic component are electrically connected to the one or more contact pads. Additionally or alternatively, however, the at least one electronic component may indirectly be attached to the interconnect device, such as via at least one electronic housing. Thus, the at least one electronic housing may be attached to the interconnect device. Still, an electrical contact between the at least one electronic component and the interconnect device may be made, such as via at least one contact passing through the electronic housing. The electronic housing may fully or partially surround the at least one electronic component. As an example, the electronic housing may comprise at least one lower electronic housing component attached to the interconnect device, wherein the at least one electronic devices inserted into the lower electronic housing component on a side opposing the interconnect device. The at least one electronic housing may further comprise at least one further electronic housing component, such as at least one upper electronic housing component, which, in conjunction with the lower electronic housing component, may form an encapsulation which fully or partially surrounds the electronic component. Additionally or alternatively, however, other types of encapsulation of the at least one electronic component may be used, such as encapsulation by using one or more casting and/or potting compounds. Thus, as an example, the lower electronic housing component may be used for receiving the at least one electronic component, wherein the upper shell or protection above the electronic component is created by using a casting and/or potting, such as by using one or more of an epoxy, a thermoplastic polymer, a rather, a silicone, and epoxies or the like. Additionally or alternatively, no electronic housing component may be used at all, such as by directly placing the at least one electronic component onto the interconnect device.

Similarly, the at least one optional energy reservoir, such as at the at least one battery, may directly or indirectly be attached to the at least one interconnect device. Thus, again, the at least one energy reservoir may fully or partially be encapsulated by at least one energy reservoir housing. Again, the at least one energy reservoir housing may comprise one or more components, such as a lower energy reservoir housing component placed onto the interconnect device, configured for receiving the at least one energy reservoir. As an upper protection, either an upper energy reservoir housing such as an upper cover may be used or, additionally or alternatively, a casting or potting. In both cases, the energy reservoir may electrically be connected via the at least one interconnect device with the at least one electronic component. Thus, generally, in this embodiment or other embodiments, the at least one interconnect device may comprise one or more electrical traces for electrically connecting the optional energy reservoir with the at least one electronic component, directly or indirectly.

As further used herein, the term "electronic component" generally refers to an arbitrary element or combination of elements which fulfill at least one electrical or electronic purpose. Specifically, the at least one electronic component may be or may comprise at least one component selected from the group consisting of an integrated circuit, an amplifier, a resistor, a transistor, a capacitor, a diode or an arbitrary combination thereof. The at least one electronic component specifically may be or may comprise at least one device capable of controlling the analyte sensor, in order to perform at least one analytical measurement with the analyte sensor. Specifically, the at least one device may comprise at least one voltage measurement device and/or at least one current measurement device. Other setups or embodiments are feasible. The at least one electronic component, as an example, may comprise at least one application-specific integrated circuit (ASIC).

As described above, the analyte sensor is operably connected to the electronics unit. The term "operably connected" may specifically refer to a state, wherein two or more objects are connected to each other such that they can interact with each other. Specifically, the analyte sensor may be operably connected to the electronics unit such that sensor signals of the analyte sensor may be transmitted to the electronics unit. Thus, the term "operably connected" may also refer to an electrically conductive connection. The analyte sensor may be electrically connected to the interconnect device, preferably via at least one of a soldering connection, a welding connection, an electrical bonding, a conductive adhesive material or a plug connection. The interconnect device may be fixedly positioned within the electronics compartment of the housing.

As generally used herein, the term "housing" may generally refer to an arbitrary element which is adapted to fully or partially surround and/or receive one or more elements in order to provide one or more of a mechanical protection, a mechanical stability, an environmental protection against moisture and/or ambient atmosphere, a shielding against electromagnetic influences or the like. Thus, the housing may simply provide a basis for attachment and/or holding one or more further components or elements. Additionally or alternatively, the housing may provide one or more interior spaces for receiving one or more further components or elements. The housing may specifically be manufactured by injection molding. However, other embodiments are feasible.

As used herein, the term "compartment" may generally refer to an arbitrary subpart of a superior element creating a partially or fully enclosed space that may be usable to contain and/or store objects. The subpart may specifically be completely or at least to a large extend closed such that an interior of the compartment may be isolated from a surrounding environment. Exemplarily, the compartment may be separated from other parts of the superior element by one or more walls. Thus, within the housing, two or more compartments may be comprised which may fully or partially be separated from one another by one or more walls of the housing. Each compartment may comprise a continuous space or lumen configured for receiving one or more objects. The housing, however, may also fully or partially be embodied by using one or more deformable materials, in a deformable state and/or in a hardened or a cured state.

As described above, the sensor compartment forms a sealed compartment. The term "sealed compartment" may refer to a property of a compartment of being isolated from a surrounding environment such that a transfer of gas, fluids and/or solid elements is completely or at least to a large extent reduced. Specifically, the sensor compartment may be configured to provide a sterile packaging for the insertable portion of the analyte sensor. Exemplarily, the detachable lower cap may be a sterile cap configured to provide sterile packaging for the insertable portion of the analyte sensor, such that the insertable portion is sealed against a surrounding environment. The term "sterile" may generally refer to a property of an arbitrary object of being at least to a large extent free from all forms of life and/or other biological agents such as prions, viruses, fungi, bacteria or spore forms. Thus, the sterile object may be treated by at least one sterilization process that eliminates and/or deactivates the forms of life and/or the other biological agents. The sterilization process may comprise one or more of the following techniques: heating, chemical treatment, irradiation, high pressure, filtration. However, other techniques are feasible. The sterilization process may be conducted within a specified region or area of the object such as a surface of the object.

As will be outlined in further detail below, the sensor compartment may comprise at least one intermediate component. The term "intermediate component" may refer to an arbitrary compartment between at least two other compartments and/or which may be located in at least one other compartment. Thus, the intermediate component may be located in the sensor compartment. The upper cap and the lower cap may be attached to the intermediate component and/or may be attached to each other, in a detachable fashion. The intermediate component may be located in between the upper cap and the lower cap. The interconnect device, as will be outlined in further detail below, may be attached to the intermediate component or vice versa.

The term "cap" may refer to an arbitrary element which is configured to close or to seal a volume. Specifically, the cap may close or seal an opening of an arbitrary container. The terms "upper cap" and "lower cap" may be considered as description without specifying an order and without excluding a possibility that several kinds of upper caps and lower caps may be applied. The term "detachable" may refer to a property of an element of being removable from an arbitrary object. Thereby, a close bonding or contact between the element and the object may be disconnected. Generally, the element may be removable in a reversible manner wherein the element may be attachable and detachable from the object or in an irreversible manner wherein the element may not be attachable to the object after detachment. Specifically, as will be outlined in further detail below, the detachable upper cap and/or the detachable lower cap may be connected to one another and/or to the intermediate component via at least one predetermined breaking point, such as via at least one predetermined breaking point having a weakening in the wall of the housing in order to allow for a simple and well-defined detachment of the caps by hand, such as at least one predetermined breaking point comprising one or more grooves, notches or slots in the wall. Alternatively, instead of using a predetermined breaking point, other types of detachable connections may be used, such as a screwing connection.

The detachable upper cap and/or the detachable lower cap may exemplarily have an elongate shape and provide an interior volume. The detachable upper cap and/or the detachable lower cap may have one or more handles allowing for a user to detach the respective cap. The detachable upper cap and the detachable lower cap may be detachably connected to the intermediate component. Specifically, the detachable upper cap and the detachable lower cap may be detachably connected to the intermediate component on opposing sides of the intermediate component. Alternatively, the detachable upper cap and the detachable lower cap may be detachably connected to one another, with the intermediate component in between. Specifically, the detachable upper cap may partially surround the insertion cannula. The insertion cannula may be fixedly attached to the detachable upper cap.

As outlined above, the detachable upper cap may be detachably connected to the intermediate component, such as at at least one upper predetermined breaking point. Additionally or alternatively, the detachable lower cap may be detachably connected to the intermediate component at at least one lower predetermined breaking point. As further used herein, the term "predetermined breaking point" may refer to an arbitrary part of an element being configured to break during mechanical load while other parts of the element remain undamaged. Specifically, the predetermined breaking point may comprise at least one notch wherein a thickness of the element may be smaller in comparison to other parts of the element. The upper predetermined breaking point and the lower predetermined breaking point may specifically be ring-shaped breaking points. The terms "upper breaking point" and "lower breaking point" may be considered as description without specifying an order and without excluding a possibility that several kinds of upper breaking points and lower breaking points may be applied. Additionally or alternatively, instead of using one or more predetermined breaking points, other types of detachable connections may be used, such as one or more screwing connections.

The sensor compartment may comprise at least one sealed opening, such as for leading a portion of the analyte sensor out of the sensor compartment, in order to be operably connected to the electronics unit, such as to the interconnect device and/or to the at least one electronic component attached thereto. The term "sealed" may generally refer to a property of an arbitrary element of being completely or at least to a large extent isolated from a surrounding environment. The sealed opening may comprise at least one sealing element. The term "sealing element" may generally refer to an arbitrary element which is configured to cover one or more elements to be sealed off from environmental influences such as moisture. The sealing element may seal the sensor compartment. Exemplarily, the sealing element may comprise at least one sealing lip. As used herein, the term "sealing lip" may refer to a maximum in a cross-sectional profile of the sealing element, which, when the sealing element thereon is pressed on another surface, is the first part of the sealing element to contact the other surface. The profile itself may be symmetric or asymmetric in shape, wherein an asymmetric profile may be favorable. The sealing element may comprise at least one sealing material, particularly a deformable sealing material, more preferably an adhesive material. The analyte sensor may pass through the sealed opening. The analyte sensor may be partially received in the sensor compartment. Specifically, the insertable portion may be at least partially received in the sensor compartment. The at least one sealed opening specifically may fully or partially be part of or fully or partially be integrated in the intermediate component. Thus, the intermediate component, as an example, may fully or partially be made of a deformable or flexible material, such as of at least one elastomeric material.

The interconnect device generally may have an arbitrary shape. Thus, as outlined above, the interconnect device specifically may be a flat device, having a flat base. The flat base may directly or indirectly be attached to the skin of the user. Thus, as an example, the interconnect device may comprise an upper side and a lower side, specifically a flat lower side, wherein the lower side comprises at least one adhesive element for attachment of the interconnect device to the skin of the user. Thus, as an example, at least one adhesive may directly or indirectly be applied to the lower side. Additionally or alternatively, at least one plaster or adhesive strip may be attached directly or indirectly to the lower side, with an adhesive surface facing the skin of the user. The lower side specifically may be a side from which the analyte sensor protrudes from the medical device.

The cross-section of the interconnect device, such as the cross-section of the flat base, however, may be adapted to the handling steps for insertion. Specifically, the interconnect device, such as the flexible interconnect device and more specifically the flexible printed circuit board, may have a noncircular shape, with one or more portions. Specifically, an asymmetric shape may be used. As an example, the interconnect device may comprise a first portion, preferably a first flap, having the electronic component attached thereto, and a second portion, preferably a second flap, having an electrical energy reservoir, preferably a battery, attached thereto. The first portion or second portion, as an example, each may have an essentially circular shape, wherein the circular shape, as an example, may be broken only in a region in which the first or second portion is connected to a central portion of the interconnect device which may be connected to the housing. Thus, as an example, the interconnect device may comprise a central portion connected to the housing and one, two or more than two portions attached to the central portion. The central portion, as an example, may comprise an opening through which the housing may penetrate the interconnect device.

Thus, as an example, the interconnect device specifically may comprise one, two or more than two flaps or wings which protrude from the housing. As an example, the interconnect device may have a shape of the wings of a moth or butterfly, preferably with foldable wings which may be folded upwardly or downwardly. Thus, as an example, the first portion and the second portion may be foldable, preferably in an upwardly or downwardly fashion towards an axis of the housing. The folding specifically may be used during insertion, in order to provide a more stable grip to the medical device when pushing the insertion cannula into the body tissue of the user. Thus, as an example, the first and second portions may be folded upwardly during insertion, and, afterwards, may be folded into a flat configuration again, such as in order to be placed flatly against the skin of the user and, preferably, to be adhered to the skin of the user by at least one adhesive.

As outlined above, the interconnect device may have an opening, wherein the housing fully or partially may penetrate the interconnect device through the opening. Thus, as an example, the housing may partially be located on an upper side of the interconnect device and partially be located on a lower side of the interconnect device, such as by partially protruding upwardly from the interconnect device and partially protruding downwardly from the interconnect device. Therein, an upward direction may be a direction which faces away from the skin of the user and a downward direction may be a direction which faces the skin of the user. As outlined above, the insertion cannula may point in the downward direction.

As further outlined above, the housing may fully or partially be attached to the interconnect device. Specifically, the housing may be attached to a rim of the opening of the interconnect device. As an example, the housing may comprise an intermediate component, as outlined above, wherein the interconnect device may fully or partially be attached to the intermediate component. Thus, the intermediate component may comprise the above-mentioned rim, with the interconnect device attached thereto.

The detachable upper cap and the detachable lower cap specifically may be disposed on opposite sides of the interconnect device. As further outlined above, the housing may have at least one intermediate component disposed in between the detachable upper cap and the detachable lower cap. The intermediate component specifically may comprise a sealing ring, specifically a sealing ring which seals a connection between the upper cap and the lower cap. The detachable upper cap and the detachable lower cap may be attached to one another, preferably by a screwing mechanism, with the intermediate component located in between the detachable upper cap and the detachable lower cap.

As outlined above, the analyte sensor, such as with the insertable portion, may be located inside the sensor compartment and, with at least one other portion, such as with an interconnecting portion, may be located outside the sensor compartment, in order to be operably connected to the electronics unit, such as to the interconnect device and/or the at least one electronic component. In order to lead the analyte sensor out of the sensor compartment in a sealed fashion and in order to avoid ingression of humidity, dirt or microbial pollution, the intermediate component may comprise at least one sealed opening, wherein the analyte sensor passes through the sealed opening. The insertable portion of the analyte sensor may at least partially be received in the sensor compartment, wherein an opposing end of the analyte sensor, such as an interconnecting portion of the analyte sensor, may be attached to the electronics unit.

The intermediate component, as an example, may be made of a rigid material. Alternatively, however, the intermediate component may fully or partially be made of a deformable material, such as of a fully or partially flexible or elastic material. Thus, as an example, the at least one intermediate component may be made of an elastomeric material.

The interconnect device, as outlined above, may be connected mechanically to the intermediate component. As an example, the interconnect device may fully or partially surround the intermediate component. The intermediate component may comprise a protruding rim, wherein the interconnect device may fully or partially be connected, specifically mechanically, to the protruding rim. Generally, for mechanically connecting the interconnect device to the housing, such as to the intermediate component, any type of connection mechanism may be used. Specifically, however, the interconnect device may be connected to the housing by using a gluing or welding connection. Other connections, however, are feasible, such as form-fit or force-fit connections.

The insertion cannula specifically may fixedly be attached to the detachable upper cap. The medical device may further comprise at least one septum received in the sensor compartment, wherein the insertion cannula passes through the septum, wherein the septum is con-figured for sealing a remainder of the sensor compartment after detachment of the detachable upper cap.

The electronics unit may contain one or more electronic components attached to the interconnect device. The electronic component specifically may be configured for controlling a measurement performed with the analyte sensor. The medical electronic component specifically may contain an application-specific integrated circuit (ASIC). The electronic component specifically may contain at least one of a measurement device configured for performing an electrochemical measurement with the analyte sensor, such as at least one current measurement device and/or at least one voltage measurement device. Further, one or more of a current source and/or a voltage source may be comprised.

The detachable upper cap and/or the detachable upper cap may comprise at least one handle. As further used herein, the term "handle" may refer to an arbitrary element which may be part of an object that can be moved or used by hand. Specifically, the detachable lower cap may comprise the handle configured for enabling the user to detach the detachable lower cap from the medical device. The handle may comprise at least one hygroscopic material, preferably at least one desiccant, more preferably activated carbon.

The medical device may further comprise at least one insertion aid configured for enabling a user to drive the insertion cannula into the body tissue and to insert the insertable portion of the analyte sensor. As further used herein, the term "insertion aid" may refer to an arbitrary technical construction being configured to insert an object into another object. Therefore, the insertion aid may comprise at least one insertion mechanism. As further used herein, the term "mechanism" may refer to an arbitrary mechanism designed to transform input forces and movement into a desired set of output forces and movement. Specifically, the insertion mechanism may be configured such that the user may apply a force in a direction of insertion to the insertion cannula. Therefore, the insertion aid may be configured to facilitate a handling of the medical device by the user and/or to reduce application errors. The insertion aid may at least partially surround the housing. Further, the insertion aid may be at least partially coupled to the housing.

The insertion aid may comprise a detachable lower cover mechanically coupled to the detachable lower cap. As further used herein, the term "cover" may refer to an arbitrary element that completely or at least to a large extent closes an object. Specifically, the cover may be or may comprise a shell, particularly a half-shell, surrounding the medical device. The detachable lower cover may be configured such that a removal of the detachable lower cover removes the detachable lower cap. The insertion aid may further comprise at least one upper cover. The upper cover may be directly or indirectly coupled to one or both of the insertion cannula or the detachable upper cap, such that a movement of the upper cover against the frame drives the insertion cannula. The terms "lower cover" and "upper cover" may be considered as description without specifying an order and without excluding a possibility that several kinds of lower covers and upper covers may be applied. The insertion aid may further comprise at least one frame. The term "frame" may refer to an arbitrary element which may be configured to support other components of a physical construction. The frame may be displaceable on the skin of the user and may at least partially surround the housing. The upper cover may be movable against the frame.

In a further aspect of the present invention, a method for assembling a medical device according to any embodiment as described above or as further described below is disclosed. The methods comprise the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for assembling the medical device comprises:
a) providing at least one part of the housing, the at least one part of the housing comprising the sensor compartment with the detachable upper cap and the detachable lower cap;
b) placing the analyte sensor at least partially into the sensor compartment, wherein the analyte sensor and the at least one part of the housing provided in step a) form an intermediate product;
c) sterilizing the intermediate product; and
d) connecting the electronics unit to the intermediate product.

The housing may be manufactured by injection molding. During step b) at least one further element may be placed at least partially into the sensor compartment. The at least one further element may be selected from the group consisting of: an insertion cannula, a sealing element, particularly a septum. The method may further comprise operably connecting, specifically electronically connecting, the analyte sensor with the electronics unit.

Step c) may be conducted by at least one sterilization process based on radiation, particularly ebeam sterilization. The method may further comprise at least one step of sterilizing the electronics unit, particularly by gas sterilization.

Specifically, the method may be performed such that step c) is performed before performing step d), in order to avoid exposing the electronics unit to the radiation. Similarly, the sterilization of the electronics unit may be performed after placing the electronics unit into the electronics compartment or into the at least one part thereof, in a state in which the sensor compartment is sealed, such as by the detachable upper cap and the detachable lower cap. Consequently, for sterilizing the electronics unit, a gas sterilization may be used, such as by using ethylene oxide. Since the sensor compartment is sealed by the upper cap and the lower cap, the gas used for gas sterilizing the electronics unit may be prevented from entering the sensor compartment and, thus, may be prevented from affecting the analyte sensor or at least the insertable portion of the analyte sensor disposed therein.

By using this two-step sterilization, the specific requirements and sensitivities of the different components may be accounted for. Thus, generally, the electronics unit is sensitive against and may be damaged by high energy radiation, such as gamma rays or electron beams. Consequently, the radiation sterilization may be performed on the intermediate product, without the electronics unit being connected to the analyte sensor, in order to sterilize the analyte sensor or at least the insertable portion of the analyte sensor. Contrarily, the analyte sensor or typical sensor chemicals used therein in most cases are sensitive against and may be damaged by sterilizing gases such as ethylene oxide. Consequently, the sterilization of the electronics unit connected to the analyte sensor may be performed such that the sterilizing gas such as the ethylene oxide is prevented from interacting with the insertable portion of the analyte sensor. Consequently, the sterilization processes may be optimized independently, without taking the risk of destroying the electronics unit by radiation and without taking the risk of destroying the analyte sensor by sterilizing gas.

In a further aspect of the present invention, a method of using the medical device according to any embodiment as described above or as further described below is disclosed. The methods comprise the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method of using a medical device comprises:
I. providing the medical device;
II. removing the detachable lower cap;
III. inserting the analyte sensor into the body tissue; and
IV. removing the detachable upper cap, thereby removing the insertion cannula from the medical device.

The medical device may further comprise the at least one insertion aid comprising the at least one upper cover and the detachable lower cover as described above. Thereby, the method of using a medical device may further comprise:

i. removing the detachable lower cover, thereby removing the detachable lower cap;
ii. inserting the analyte sensor into the body by applying an insertion mechanism via the upper cover.

The housing and/or the interconnect device may comprise the at least one adhesive surface, such as an adhesive surface which may optionally be covered by at least one protective foil, wherein, such as during step i. and/or during step ii., the protective foil may be removed. Specifically, the detachable lower cover may be removed by a rotatory motion. However, other embodiments are feasible. The upper cover may comprise at least one spring drive and before conducting step i. the spring drive may be tightened thereby securing parts of the insertion mechanism, wherein after conducting step II., the insertion cannula is retracted by at least one spring.

The proposed medical device, the method for assembling a medical device and the method of using a medical device provide many advantages over known devices and methods.

Usually, common medical devices may initially comprise two components. The two components may form a final product after application of the medical device to the body tissue of the user. The analyte sensor may commonly have to be connected to the electronics unit via the user. This may specifically lead to errors during application and thus to severe consequences such as measurement errors. Therefore, in common medical devices, elaborate constructions may generally have to be realized to circumvent error sources. The elaborate constructions may exemplarily comprise sealings, electrical contacts or locking forces.

Specifically in case of analyte sensors which are electrochemical sensors, electronic components may generally not be treatable via beam sterilization. However, electrochemical sensors themselves generally may only be treatable via beam sterilization so that a functionality of the electrochemical sensor may be ensured.

Therefore, the medical device according to the present invention may comprise a combination of a sterile compartment including the analyte sensor and the electronics unit which may specifically be a single-use electronics unit. The sterile compartment may be integrated into or attached to the electronics unit.

The user may receive an "all-in-one" medical device without a need for assembling the medical device. The medical device may further be robust and low-priced. An application of the medical device to the body tissue of the user may be conductible in a simple and intuitive manner.

Parts of the medical device may remain at the body tissue of the user after using the medical device. These parts may stay at the body tissue during a predetermined application period. A sterilization of the analyte sensor and a subsequent assembling of the electronics unit during assembling the medical device may be realized without opening the sealed compartment. Further, a compact and small construction as well as a simple assembling may be possible.

During using the medical device, the housing may be opened by the user. A protective foil of the adhesive element may be removed and the detachable lower cap may be detached. The medical device may be mounted on the body tissue of the user and the analyte sensor may be inserted into the body tissue. The insertion cannula may be removed from the body tissue. Thereafter, the detachable upper cap may be detached from the medical device.

The septum may be an individual component or may be manufactured by injection molding. The barbed hook may be configured to prevent a second usage of the insertion cannula. The barbed hook may be an additional component or may be integrated as one component. The insertion cannula may be a tube or a stamped-bent part. The insertion cannula may be sealed by the septum. Therefore, the insertion cannula may specifically have a round cross-section. However, other embodiments such as a flat design are feasible.

The insertion aid may comprise the upper cover. The upper cover may be part of the primary packaging. Further, the user may use the upper cover for using the medical device. The upper cover may be fixedly connected to the detachable upper cap. The insertion aid may have the retraction mechanism configured to retract the insertion cannula automatically after the insertion cannula has been inserted into the body tissue. The detachable lower cover of the insertion aid may be part of the primary packaging. Further, the detachable lower cover may be fixedly connected to the detachable lower cap. During opening of the detachable lower cover, the detachable lower cap may be opened at the same time and the adhesive surface may be exposed. The frame may protect the insertion cannula, specifically before using the medical device. The user may hold the medical device onto the body tissue. The frame may require an initial force such that the user may build up a force during manually inserting the insertion cannula and may insert quickly. The frame may trigger a mechanism such that the insertion cannula may be withdrawn automatically as soon as the frame is compressed. Specifically, the mechanism may be a spring-pretensioned mechanism. The insertion aid may provide an easy handling for the user.

The detachable lower cover may comprise a basis which is fixedly connected to a lower part of the detachable lower cap, exemplarily via a snap connection, an adhesive bonding and/or a longitudinal guide or transferring force. The basis may comprise gripping surfaces for detaching the detachable lower cover. The basis may at the same time be a cover for the adhesive surface. This may lead to an extended shelf-life of the adhesive surface. By detaching of the detachable lower cover, the detachable lower cap may be opened, the insertion cannula and the analyte sensor may be exposed and the adhesive surface may be exposed at the same time.

The upper cover of the insertion aid may comprise the spring drive. The spring drive may be configured to trigger the insertion of the insertion cannula. The spring drive may be tensioned during pressing the electronics unit into the insertion aid. The insertion cannula may click into an element which may trigger a withdrawing of the insertion cannula after insertion.

The upper cover may comprise guiding elements such that a circulation of the electronics unit within the insertion aid is at least to a large extent suppressed. Exemplarily, the electronics unit may have a non-round shape, there may be guiding rails in an external shape of the electronics unit and/or there may be special structures such as nuts within the electronics unit.

The insertion aid may be triggered via a release button. The medical device may be shot on the body tissue. At a bottom dead center the spring drive may be released for withdrawing the insertion cannula. The insertion aid may be removed from the body tissue. The user may optionally detach the detachable upper cap with the insertion cannula by hand. Optionally, the user may tilt the insertion aid thereby detaching the detachable upper cap.

A tensioning of the medical device may be realized via a rotational movement. Thereby, the housing may be turned on and may be hold up from below. This may exemplarily be realized by a suitable formed primary packaging. Thereby, the primary packaging may be coupled with the detachable lower cap. Exemplarily, the insertion aid may be configured to conduct the rotational movement for detaching the detachable lower cap by itself. This may be realized as follows: During tensioning of the medical device, two mechanisms may be tensioned. A first mechanism may refer to a spring system for inserting the analyte sensor into the body tissue as described above. A second mechanism may refer to the rotational movement as described above. The electronics unit may be fixed at a top dead center within the insertion aid. As soon as the electronics unit may be fixed, there may be a rotational movement in a counter direction.

Alternatively, other mechanisms may be applied to remove the detachable upper cap from the electronics compartment such as a coupled mechanism which may be withdrawable in an easy manner, cutting a breaking point with a knife or turning off the detachable upper cap. The detachable upper cap does not need to be fixedly connected to the electronics compartment. To facilitate assembling of the medical device and/or to facilitate removing the detachable upper cap by the user, the couple mechanism may be applied. Exemplarily, a tube-in-tube-system may be applied comprising a sealing with an elastic mass such as rubber, thermoplastic polymers, an epoxy or silicone.

By using a flexible interconnect device, such as a flexible printed circuit board, the at least one electronic component may be applied to a flexible, bendable part and, consequently, may be in a less spacey state as compared to the electronics unit with the analyte sensor inserted into the body tissue and the electronics unit flatly resting on the skin of the user.

During the insertion process, when the whole medical device is pressed onto the skin and when the sensor is inserted into the body tissue, the skin may distort and bulge inwardly, at the insertion site. In case the skin is not held in place by a stiff device, such as a body mount including a plaster, the insertion depth may, thus, vary, depending on the bulging of the skin. By deforming the electronics unit during insertion, such as by folding the flaps upwardly, a more constant insertion depth may be achieved.

Further, the use of a flexible interconnect device such as a flexible printed circuit board may increase the comfort of wearing the medical device and the analyte sensor inserted into the body tissue. Additionally, a stiff body mount is more prone to losing contact with and detaching from the skin of the user. A flexible system, contrarily, may move with the movement of the skin and provides a lower surface for mechanical influences. Consequently, the stability of the device is increased as compared to conventional devices.

Thus, generally, during step VII. of the method of using the medical device, the at least two portions of the interconnect device, such as the at least two flaps, may be folded or bent upwardly. After insertion, the at least two portions may be folded back, in order to rest flatly on the skin of the user. This foldable medical device generally may lead to a compact medical device which may easily be manufactured. The user may obtain a completely manufactured continuous monitoring system without need for further assembly, as compared to e.g. a system which requires an establishment of electrical connections by the user, such as by using one or more plugs. The risk of failure during application of the analyte sensor thereby is greatly reduced. Further, the medical device may be designed as a compact system for insertion. Further, the robustness may be increased, and the cost of the medical device may be reduced due to a lowering of the number of parts required for the medical device.

Further, a part of the housing may remain on the body of the user after insertion. Thus, as outlined above, an intermediate component may remain on the skin of the user, after detaching the lower and upper cap and after insertion of the analyte sensor.

The at least one electronic component may fully or partially be encapsulated. Thus, as outlined above, an encapsulation may even be provided in a soft fashion, by using soft materials for encapsulating the at least one electronic component. Thus, the at least one electronic housing may fully or partially be made of at least one flexible or deformable or soft material. As an example, rubber, silicone, a thermoplastic polymer, or other soft materials may be used, which further increases the comfort of wearing the medical device.

By using an insertion aid, such as an insertion aid comprising the at least one housing and/or the at least one upper cap and/or the insertion cannula, the electronics unit may be designed in a small fashion during insertion, wherein, afterwards, by flapping down the portions of the interconnect device, the electronics unit may be mounted to the skin of the user, e.g. without opening a sterile range. Consequently, a compact system and a simple mounting and insertion may be realized.

Summarizing, the following embodiments are potential embodiments of the present invention. Other embodiments, however, are feasible.

Embodiment 1: A medical device for detecting at least one analyte in a body fluid, the medical device comprising:
  at least one analyte sensor having an insertable portion adapted for at least partially being inserted into a body tissue of a user,
  at least one insertion cannula, wherein the analyte sensor at least partially is placed inside the insertion cannula;
  at least one housing, wherein the housing comprises at least one sensor compartment, wherein the sensor compartment forms a sealed compartment receiving at least the insertable portion of the analyte sensor, wherein the sealed compartment comprises at least one detachable upper cap and at least one detachable lower cap, wherein the detachable lower cap is configured for detachment before insertion, thereby opening the insertable portion for insertion, wherein the insertion cannula is attached to the detachable upper cap, wherein the detachable upper cap is configured for detachment after insertion, thereby removing the insertion cannula; and
  at least one electronics unit, wherein the analyte sensor is operably connected to the electronics unit, wherein the electronics unit comprises at least one interconnect device with at least one electronic component attached thereto, wherein the interconnect device fully or partially surrounds the housing.

Embodiment 2: The medical device according to the preceding embodiment, wherein the interconnect device comprises a printed circuit board.

Embodiment 3: The medical device according to any one of the preceding embodiments, wherein the interconnect device comprises a flexible printed circuit board.

Embodiment 4: The medical device according to the preceding embodiment, wherein the flexible printed circuit board is fully or partially made of polyimide.

Embodiment 5: The medical device according to any one of the preceding embodiments, wherein the interconnect device comprises an upper side and a lower side, wherein the lower side comprises at least one adhesive element for attachment of the interconnect device to the skin of the user.

Embodiment 6: The medical device according to any one of the preceding embodiments, wherein the interconnect device comprises a first portion, preferably a first flap, having the electronic component attached thereto, and a second portion, preferably a second flap, having an electrical energy reservoir, preferably a battery, attached thereto.

Embodiment 7: The medical device according to the preceding embodiment, wherein the first portion and the second portion each have an essentially circular shape.

Embodiment 8: The medical device according to any one of the two preceding embodiments, wherein the interconnect device has the shape of the wings of a moth or butterfly.

Embodiment 9: The medical device according to any one of the three preceding embodiments, wherein the first portion and the second portion are foldable, preferably in an upwardly or downwardly fashion towards an axis of the housing.

Embodiment 10: The medical device according to any one of the preceding embodiments, wherein the interconnect device has an opening, wherein the housing fully or partially penetrates the interconnect device through the opening.

Embodiment 11: The medical device according to the preceding embodiment, wherein the housing is attached to a rim of the opening of the interconnect device.

Embodiment 12: The medical device according to any one of the preceding embodiments, wherein the detachable upper cap and the detachable lower cap are disposed on opposite sides of the interconnect device.

Embodiment 13: The medical device according to any one of the preceding embodiments, wherein the sensor compartment comprises at least one intermediate component disposed in between the detachable upper cap and the detachable lower cap.

Embodiment 14: The medical device according to the preceding embodiment, wherein the intermediate component comprises a sealing ring.

Embodiment 15: The medical device according to any one of the two preceding embodiments, wherein the detachable upper cap and the detachable lower cap are attached to one another, preferably by a screwing mechanism, with the intermediate component located in between the detachable upper cap and the detachable lower cap.

Embodiment 16: The medical device according to any one of the three preceding embodiments, wherein the intermediate component comprises at least one sealed opening, wherein the analyte sensor passes through the sealed opening.

Embodiment 17: The medical device according to the preceding embodiment, wherein the insertable portion of the analyte sensor at least partially is received in the sensor compartment, wherein an opposing end of the analyte sensor is attached to the electronics unit.

Embodiment 18: The medical device according to any one of the four preceding embodiments, wherein the intermediate component is fully or partially made of a deformable material, preferably of a flexible or an elastic material.

Embodiment 19: The medical device according to any one of the five preceding embodiments, wherein the interconnect device is connected to the intermediate component.

Embodiment 20: The medical device according to the preceding embodiment, wherein the interconnect device at least partially surrounds the intermediate component.

Embodiment 21: The medical device according to any one of the two preceding embodiments, wherein the intermediate component comprises a protruding rim, wherein the interconnect device is connected to the protruding rim.

Embodiment 22: The medical device according to any one of the preceding embodiments, wherein the insertion cannula is fixedly attached to the detachable upper cap.

Embodiment 23: The medical device according to any one of the preceding embodiments, wherein the medical device further comprises at least one septum received in the sensor compartment, wherein the insertion cannula passes through the septum, wherein the septum is configured for sealing a remainder of the sensor compartment after detachment of the detachable upper cap.

Embodiment 24: The medical device according to any one of the preceding embodiments, wherein the electronics unit contains a single electronic component attached to the interconnect device, wherein the electronic component is configured to control a measurement performed with the analyte sensor.

Embodiment 25: The medical device according to the preceding embodiment, wherein the electronic component contains an application-specific integrated circuit.

Embodiment 26: The medical device according to any one of the two preceding embodiments, wherein the electronic component contains at least one of a measurement device configured for performing an electrochemical measurement with the analyte sensor.

Embodiment 27: Method for assembling a medical device according to any one of the preceding embodiments, wherein the method comprises:
  a) providing at least one part of the housing, the at least one part of the housing comprising the sensor compartment with the detachable upper cap and the detachable lower cap;
  b) placing the analyte sensor at least partially into the sensor compartment, wherein the analyte sensor and the at least one part of the housing provided in step a) form an intermediate product;
  c) sterilizing the intermediate product; and
  d) connecting the electronics unit to the intermediate product.

Embodiment 28: The method according to the preceding embodiment, wherein step c) comprises a radiation sterilization.

Embodiment 29: The method according to any one of the two preceding embodiments, the method further comprising at least one step of sterilizing the electronics unit.

Embodiment 30: The method according to the preceding embodiment, wherein the step of sterilizing the electronics unit comprises a gas sterilization.

Embodiment 31: Method of using the medical device according to any one of the preceding embodiments referring to a medical device, the method comprising:
  I. providing the medical device;
  II. removing the detachable lower cap;
  III. inserting the analyte sensor into the body tissue; and
  IV. removing the detachable upper cap, thereby removing the insertion cannula from the medical device.

SHORT DESCRIPTION OF THE FIGURES

Further details of the invention may be derived from the following disclosure of preferred embodiments. The features of the embodiments may be realized in an isolated way or in any combination. The invention is not restricted to the embodiments. The embodiments are schematically depicted in the figures. Identical reference numbers in the figures refer to identical elements or functionally identical elements or elements corresponding to each other with regard to their functions.

DETAILED DESCRIPTION OF THE EMBODIMENTS

Figure 1:
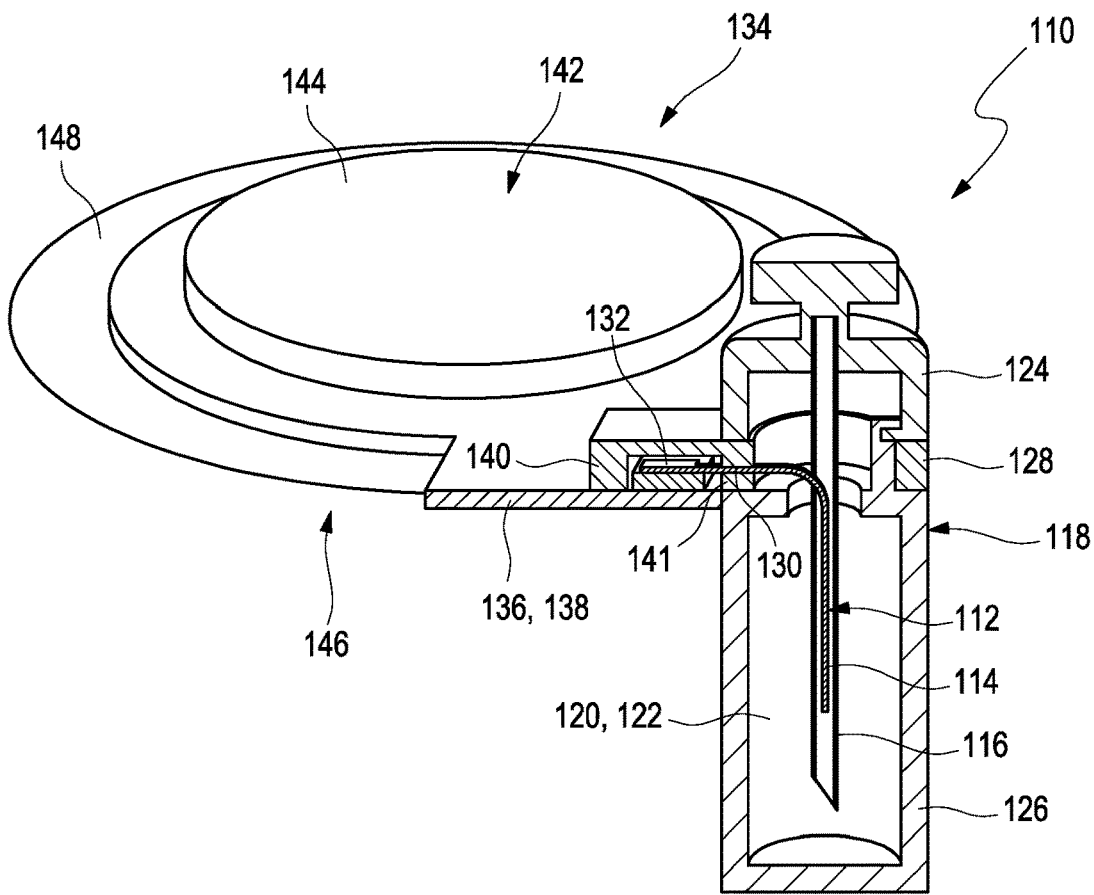
FIG. 1 shows a cross-sectional view of a first embodiment of a medical device.

In FIG. 1, a cross-sectional view of a first embodiment of a medical device 110 for detecting at least one analyte in a body fluid is shown. The medical device 110 comprises an analyte sensor 112, which, as an example, may be embodied as flexible analyte sensor and which preferably is embodied as an electrochemical analyte sensor. The analyte sensor 112 comprises an insertable portion 114 which is configured for insertion into a body tissue of a user.

The medical device 110 further comprises an insertion cannula 116, which, as an example, may be embodied as a slotted insertion cannula 116. Other types of insertion cannulae are feasible, too. The insertable portion 114 of the analyte sensor 112 is located inside the insertion cannula 116.

The medical device 110 further comprises a housing 118, enclosing a sensor compartment 120. The sensor compartment 120 forms a sealed compartment 122 which is sealed against an environment of the medical device 110. The sealed compartment 122 receives the insertable portion 114 of the analyte sensor 112 and, further, may receive the insertion cannula 116.

The housing 118, such as the sealed compartment 122, comprises a detachable upper cap 124 and a detachable lower cap 126. The detachable upper cap 124 and the detachable lower cap 126 may be connected to one another, such as by a screwing mechanism. Alternatively, however, the detachable upper and lower cap 124, 126 may detachably be connected to other components of the housing 118.

The housing 118 may further comprise an intermediate component 128, which, preferably, may have the shape of a ring and/or which may surround the insertion cannula 116 in a ring-shaped fashion. The intermediate component 128 may comprise a sealed opening 130 through which the analyte sensor 112 is guided out of the sealed compartment 122, such that a connection portion 132 of the analyte sensor 112 is located outside the sealed compartment 122. The intermediate component 128, as an example, may fully or partially be made of a deformable or flexible material forming a sealing between the upper cap 124 and the lower cap 126. As an example, the intermediate component 128 may fully or partially be made of an elastomeric material such as a rubber and/or a silicone.

The medical device 110 further comprises at least one electronics unit 134. The electronics unit 134 comprises an interconnect device 136 which, preferably, is fully or partially embodied as a flexible printed circuit board 138. The interconnect device 136 may comprise, which is not show in the figures, one or more conductive traces and/or one or more contact portions such as contact pads. As an example, the connection portion or contact portion 132 of the analyte sensor 112 may electrically be connected to one or more of the electrical traces and/or contact pads of the interconnect device 136, in order to electrically contact the analyte sensor 112. Thus, as an example, the intermediate component 128 may comprise one or more protrusions 140 which simply may support the connection portion or contact portion 132 of the analyte sensor 112 and/or which e.g. may press the connection portion or contact portion 132 of the analyte sensor 112 onto the interconnect device 136, such as onto one or more contact pads of the interconnect device 136 and/or onto one or more conductive traces. The protrusion 140 may comprise a rim 141 which fully or partially surrounds a region in which the analyte sensor 112 is electrically connected to the interconnect device 136. Further, a soldering and/or a conductive adhesive may be used for electrically connecting the analyte sensor 112 with the interconnect device 136.

The electronics unit 134 further comprises at least one electronic component 142 which may directly or indirectly be applied to the interconnect device 136. As will be outlined in further detail below, the at least one electronic component 142 may fully or partially be encapsulated, such as by one or more electronic housings 144.

The interconnect device 136 may comprise at least one adhesive surface. Thus, as an example, the medical device 110, on a side of the interconnect device 136 facing a skin of the user, also referred to as a lower side 146, may comprise at least one adhesive element 148 and/or at least one adhesive surface, such as a plaster. On the lower side 146, the plaster may comprise at least one removable liner which may be removed before adhesion to the skin of the user.

For manufacturing the medical device 110 as shown in FIG. 1, firstly, the housing 118 with the insertion cannula 116 and the analyte sensor 112 at least partially disposed therein may be provided. Further, the interconnect device 136 may be provided and, at this stage or at a later stage, the analyte sensor 112 may operably be connected to the interconnect device 136 and/or to an electronic component 142 disposed thereon. Preferably before providing an electronic component of the electronics unit 134, the analyte sensor 112 may be sterilized, such as by radiation sterilization, e.g. by electron beam sterilization. Afterwards, the at least one electronic component 112 may be applied, such as by applying the at least one electronic component 142 to the interconnect device 136. At this stage, preferably after sealing the housing 118, a further step of sterilization may be applied, in order to sterilize the electronics unit 134. For this purpose, a method of sterilization may be used which is not compatible with the insertable portion 114 of the analyte sensor 112, such as by using a gas sterilization. The sterilizing gas, however, due to the sealing properties of the housing 118 and, specifically, the sealed compartment 122, may not reach the insertable portion 114 of the analyte sensor 112. Thus, the at least one electronic component 142 and the insertable portion 114 may be sterilized independently, without detrimental influences.

Figure 2:
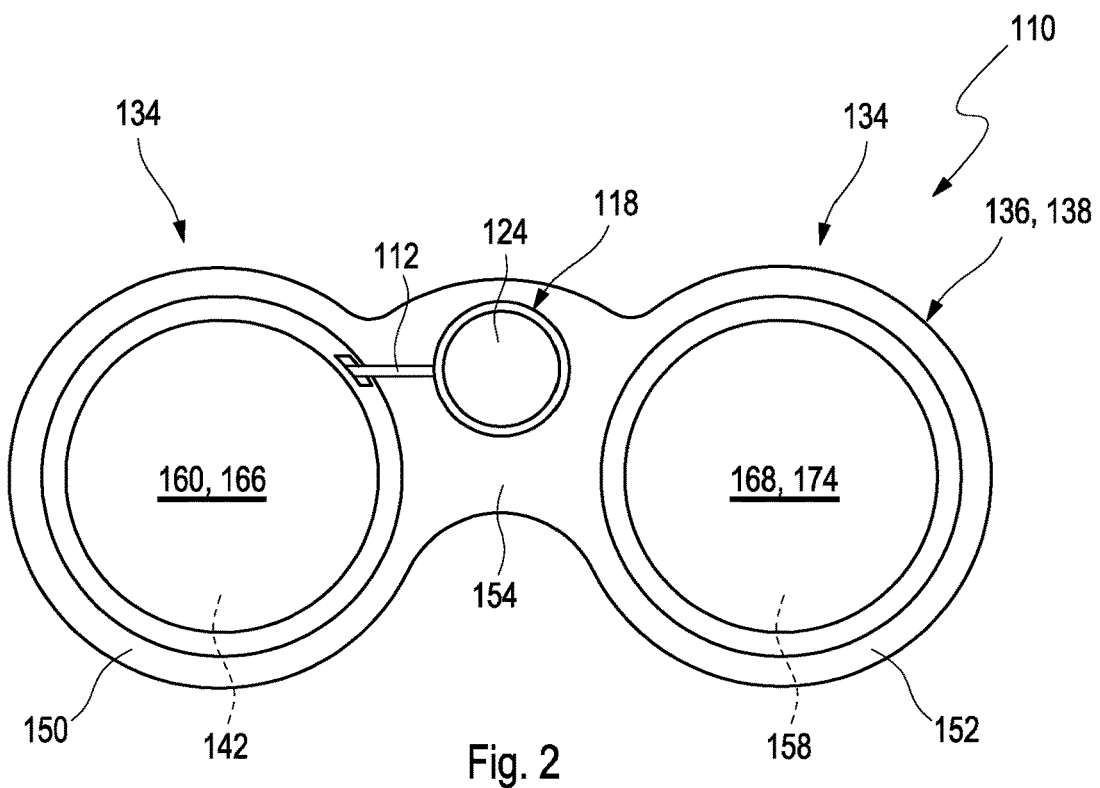
FIG. 2 shows a top view of a second embodiment of a medical device.
Figure 3:
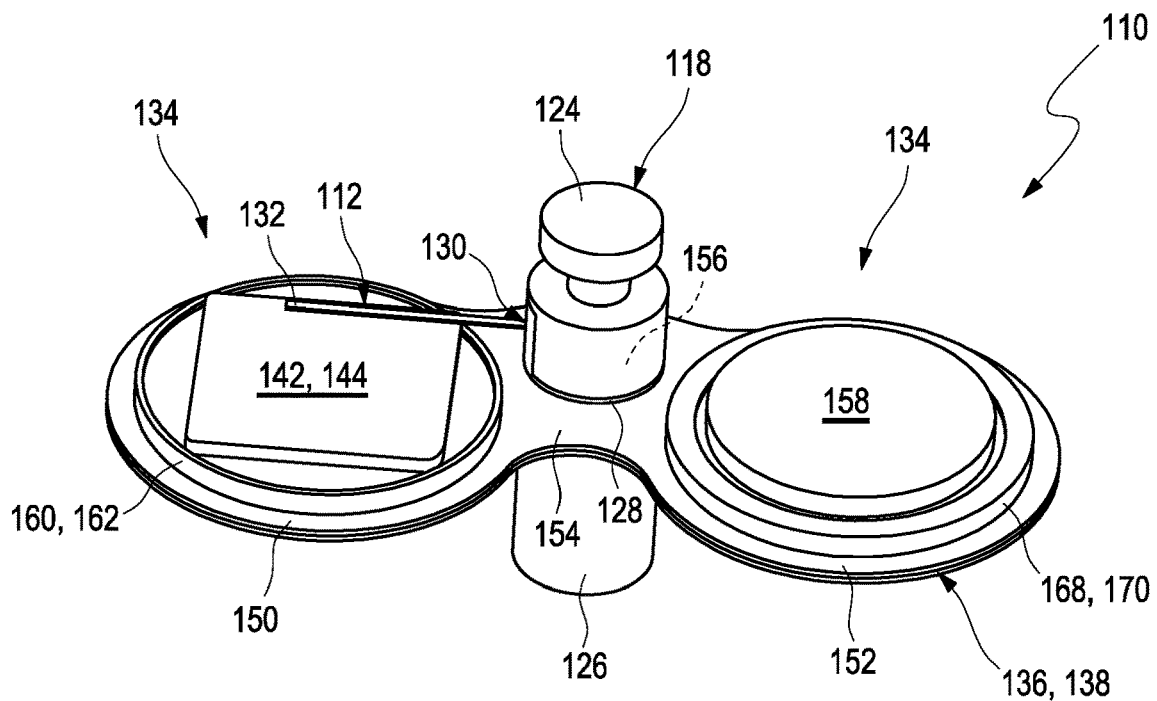
FIG. 3 shows a perspective view of the second embodiment of the medical device, with an electronic housing and an energy reservoir housing opened.
Figure 4:
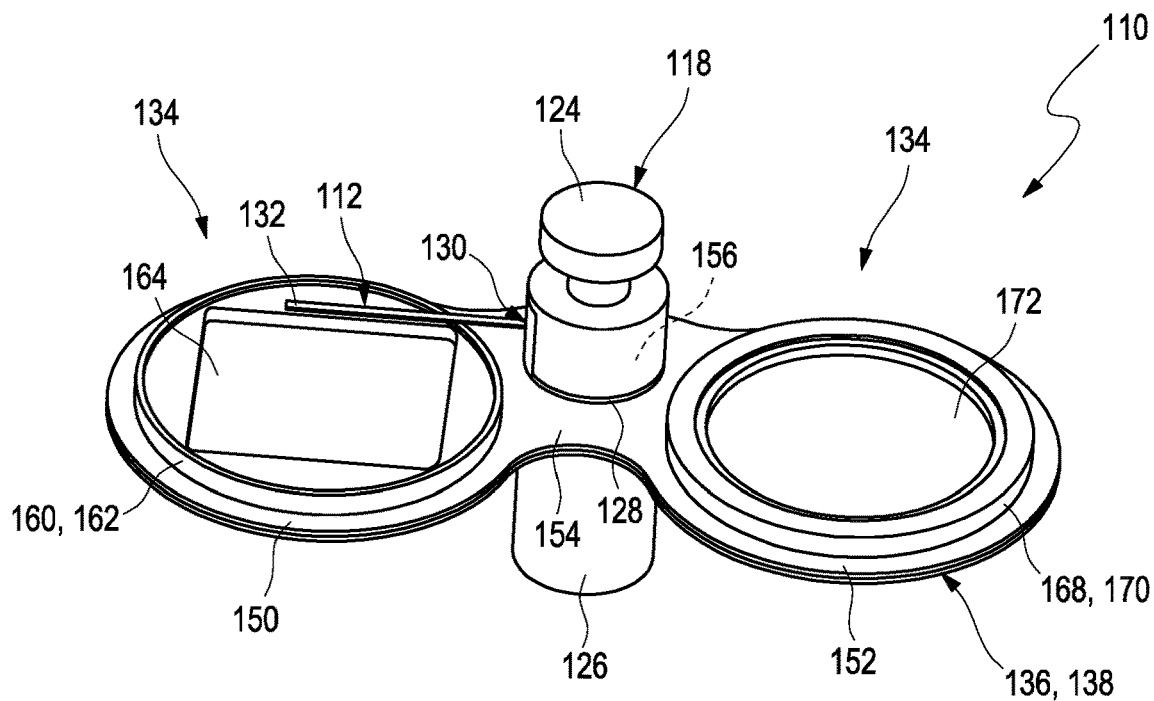
FIG. 4 shows the setup of FIG. 3 with an electronic component and an energy reservoir removed.
Figure 5:
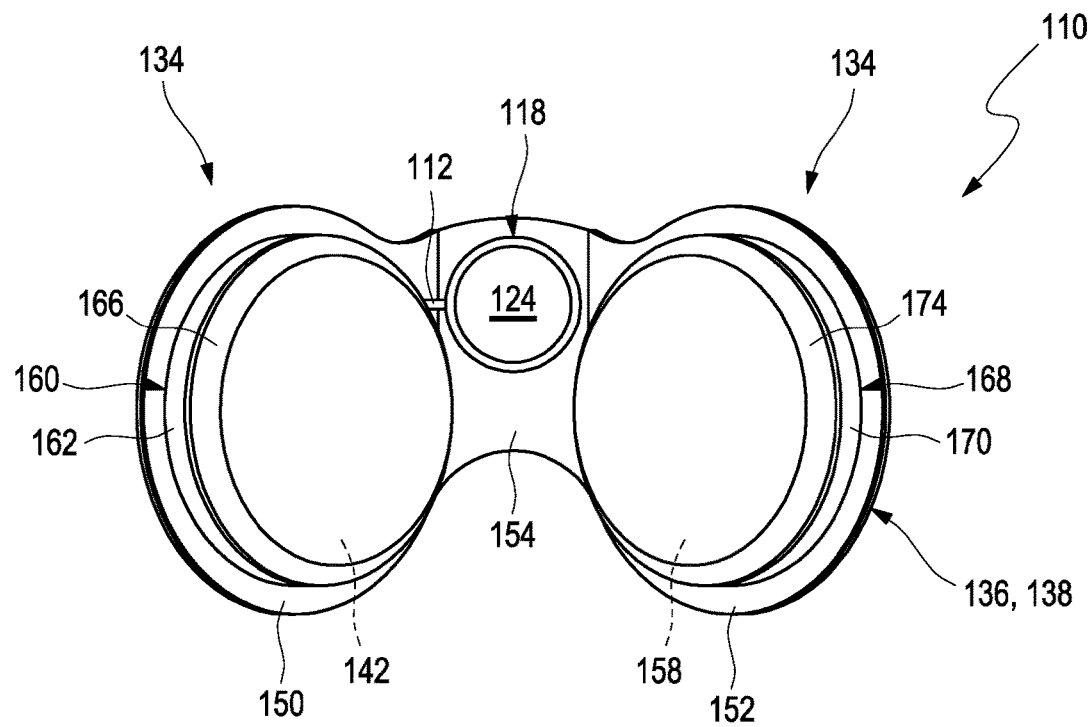
FIG. 5 shows the embodiment of FIG. 2 with a first portion and a second portion bent upwardly, in a perspective view.
Figure 6:
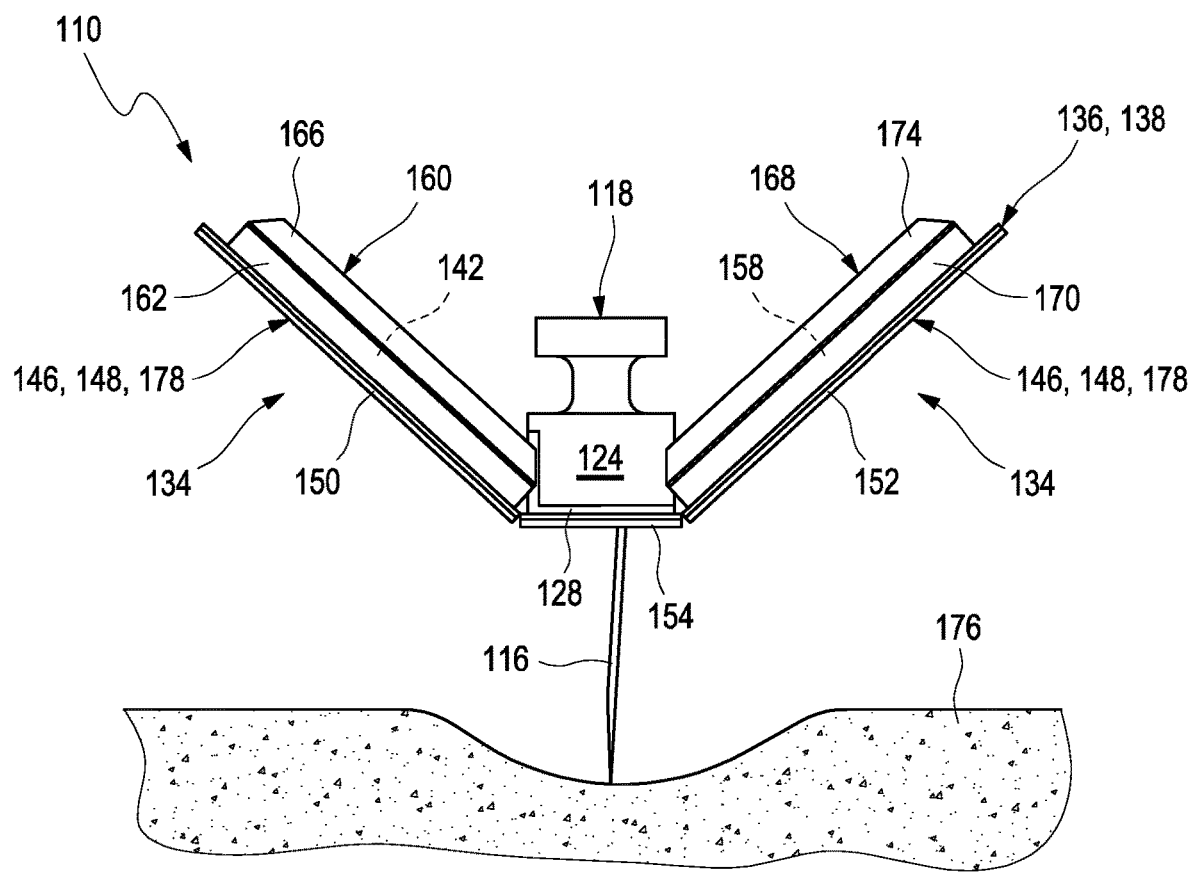
FIG. 6 shows the setup of FIG. 5 in a side view, with the lower cap removed, with the insertion cannula before insertion.
Figure 7:
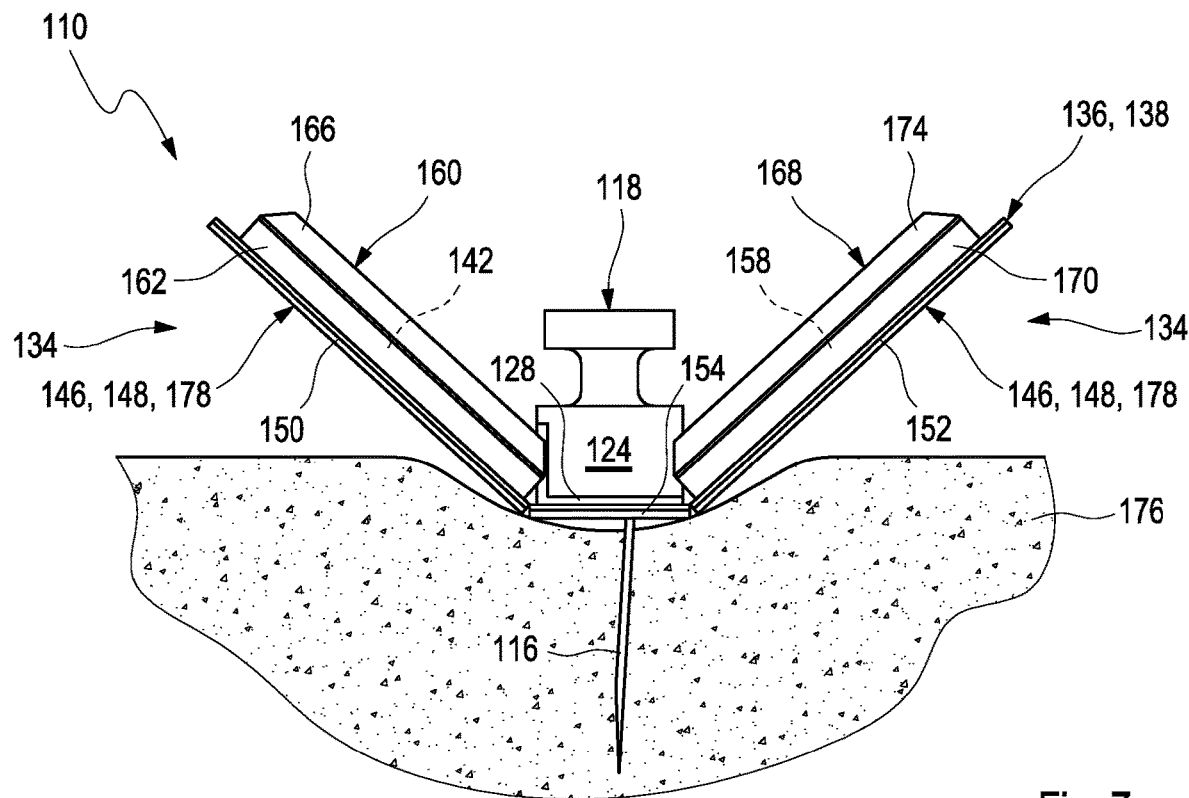
FIG. 7 shows the setup of FIG. 6 during insertion.
Figure 8:
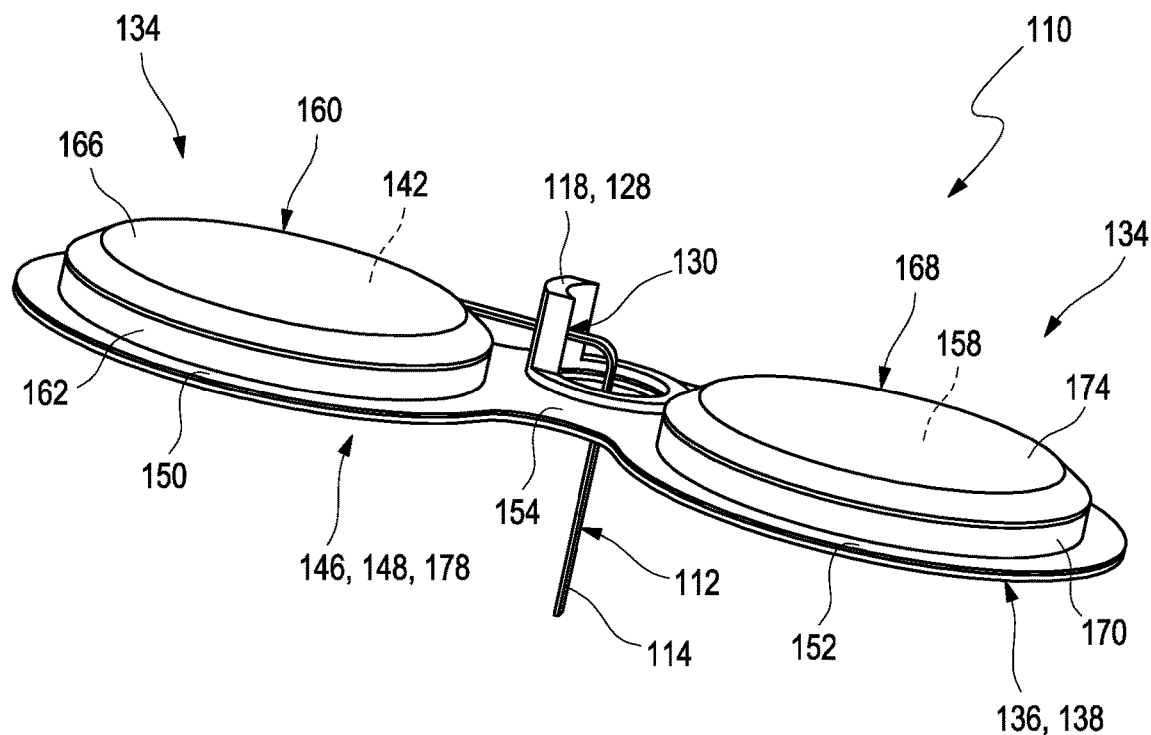
FIG. 8 shows the medical device after insertion (without the body tissue).

In FIGS. 2 to 8, a second embodiment of the medical device 110 is shown, which is widely similar to the embodiment shown in FIG. 1, except for minor differences which will be explained in further detail below. Therein, different views and different configurations of the embodiment are shown. FIG. 2 shows a top view, FIGS. 3 and 4 show perspective partial views, FIGS. 5, 6 and 7 show a folded configuration, and FIG. 8 shows a configuration with the upper and lower caps 124, 126 and the insertion cannula 116 removed and with the electronics unit 134 resting on a skin of a user (not shown), with the insertable portion 114 of the analyte sensor 112 protruding into a body tissue of the user. These different views and configurations of the second embodiment of the present invention, in the following, will be explained in conjunction. For most components and reference numbers, reference may be made to the description of FIG. 1 above.

Thus, the medical device 110 widely corresponds to the setup shown in FIG. 1. Again, an interconnect device 136 is provided, which may be embodied as a flexible printed circuit board 138. The interconnect device 136, however, in this embodiment, comprises a first portion 150, also referred to as a first flap, as well as a second portion 152, also referred to as a second flap. The first and second portions, as specifically shown in FIG. 2, preferably may have a circular shape. However, other shapes are feasible. The circular shape, however, may increase the comfort of wearing. The interconnect device 136 may further comprise a central portion 154 which connects the interconnect device 136 with the housing 118, such as, as can be seen in FIG. 3, with the intermediate component 128 of the housing 118. The central portion 154 of the interconnect device 136 may comprise an opening 156 for receiving the housing 118. The interconnect device 136 may directly or indirectly be attached to the intermediate component 128 of the housing 118, such as by using a protruding rim of the intermediate component 128 or the like.

As opposed to the setup shown in FIG. 1, the embodiment shown in FIGS. 2 to 8 shows an alternative connection between the analyte sensor 112 and the electronics unit 134. Thus, in each embodiment, the analyte sensor 112 may electrically be connected to the electronic component 142 of the electronics unit 134, as shown e.g. in FIG. 3, and/or to the interconnect device 136, as e.g. shown in the embodiment of FIG. 1. A combination of both embodiments, however, is feasible.

The embodiment shown in FIGS. 2 to 8 further shows an option in which the electronics unit 134, besides the at least one electronic component 142, comprises at least one electrical energy reservoir 158, such as a battery or the like. The at least one electronic component 142 may be disposed directly or indirectly on the first portion 150 or first flap, whereas the at least one electrical energy reservoir 158 may directly or indirectly be disposed on the second portion 152, such as the second flap. The electrical energy reservoir 158 may be electrically connected to the electric component 142 via at least one electrical trace disposed on and/or in the interconnect device 136, which is not shown in the figures.

As outlined above, the at least one electronic component 142 and/or the at least one electrical energy reservoir 158 may directly or indirectly be connected to the interconnect device 136. Specifically, as shown in the embodiment of FIGS. 2 to 8, the electronic component 142 and/or the electrical energy reservoir 158 may fully or partially be surrounded by at least one housing and/or encapsulation. Thus, in the embodiment shown in FIGS. 2 to 8, the electronic component 142 is fully or partially encapsulated by an electronic housing 160 having a lower electronic housing component 162 attached to the interconnect device 136 with a receptacle 162 therein, for receiving the electronic component 142. Inside the receptacle 164, one or more contact pads and/or one or more electrical tracers may be provided, in order to connect the electronic component 142 with the interconnect device 136. After placement of the electronic component 142 and after connection of the analyte sensor 112 to the electronic component 142, an upper electronic housing component 166 may be applied, in order to cover the electronic component 142, as can be seen when comparing the setup of FIGS. 3 and 5. However, other encapsulation techniques may be used, such as by using a casting, e.g. by using a rubber, a mold or another sealing for encapsulating the electronic component 142.

Similarly, the electrical energy reservoir 158 may fully or partially be encapsulated. Thus, as can be seen e.g. in FIGS. 3 and 4, the electronics unit 134 may comprise an energy reservoir housing 168, e.g. with a lower energy reservoir housing component 170 with a receptacle 172 therein, which may directly or indirectly be attached to the interconnect device 136, and, optionally, an upper energy reservoir housing component 174. The housings 160, 168 may fully or partially be made of rigid materials or may fully or partially be made of deformable or soft materials. Thus, again, as an example, the upper energy reservoir housing component 174 may also fully or partially be made of a deformable material, such as a moldable or castable material.

As outlined above, the interconnect device 136 preferably is fully or partially be made of a flexible or deformable material. Thus, as an example, a flexible printed circuit board 138 may be used. This allows for a handling, in which the interconnect device 136, during insertion, has a different configuration as compared to the configuration later on, with the analyte sensor 112 inserted. As an example, the foldable flaps 150, 152 may be folded upwardly, as shown e.g. in FIGS. 5 to 7. Thus, firstly, the flaps 150, 152 may be bent upwardly, and the lower cap 126 may be removed, as shown in FIG. 6. The insertion cannula 116 may pierce the skin 176 of the user, as shown in FIG. 6. An adhesive surface 178 on a lower side 146 of the medical device 110 may, firstly, get in contact with the skin 176 in the range of the central portion 154, as shown e.g. in FIG. 7. Afterwards, after insertion, the portions 150, 152 may be folded back in a horizontal position, resting on the skin 176, and adhering to the skin 176. Further, the detachable upper cap 124 with the insertion cannula 116 may be removed, thereby transforming the configuration from FIG. 7 into the configuration shown in FIG. 8, with the sensor 112 with its insertable portion 114 inserted into the body tissue and with the detachable upper cap 124 and the cannula 116 removed.

Figure 9:
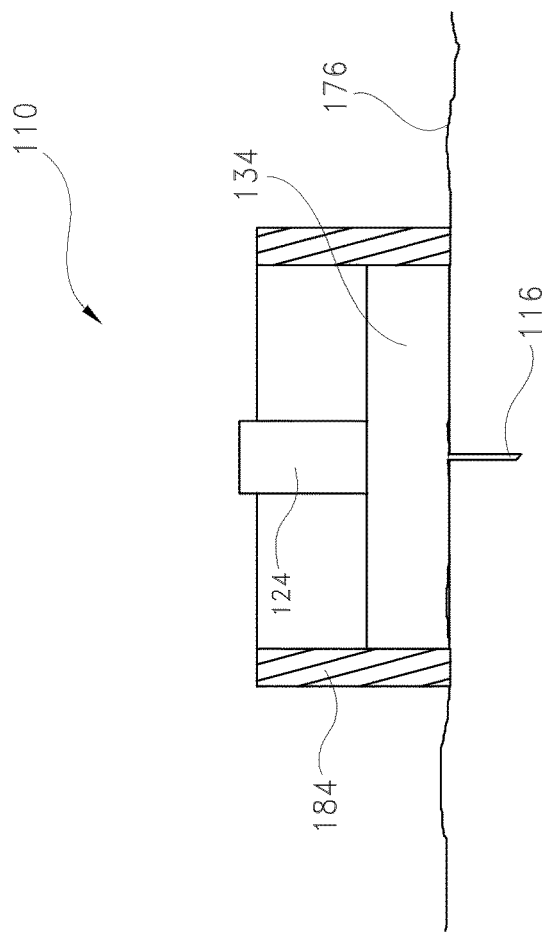
FIG. 9 shows a schematic view of an embodiment of a medical device including lower and upper caps attached to an electronics compartment and surrounded by lower and upper covers.
Figure 10:
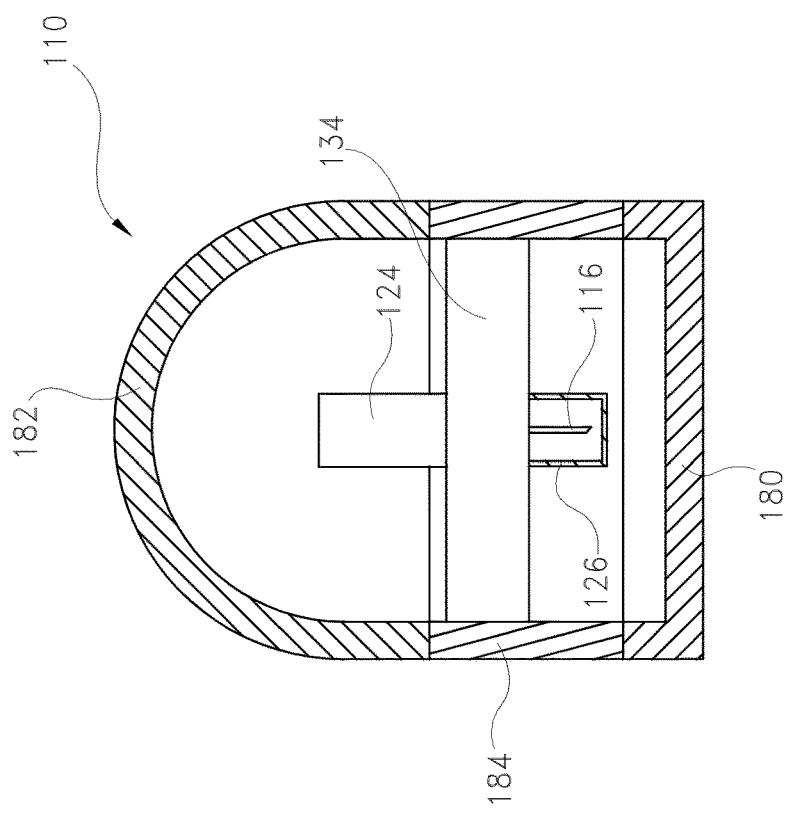
FIG. 10 shows a schematic view of the embodiment of FIG. 9 in which the lower and upper covers and the lower cap have been removed, the analyte sensor has been inserted into the user's body tissue, and the electronics compartment is resting on the skin.

FIG. 9 is a schematic view of an embodiment of a medical device in accordance with the present invention. The medical device includes lower cap 126 and upper cap 124 attached to electronics unit 134 and surrounded by lower cover 180 and upper cover 182. The electronics unit 134 is configured to slide relative to frame 184. FIG. 10 shows a schematic view of the embodiment of FIG. 9 in which the lower cap 126, the lower cover 180, and the upper cover 182 have been removed. Also in FIG. 10, the analyte sensor 116 has been inserted into the user's body tissue 176, and the electronics unit 134 is resting on the skin.

LIST OF REFERENCE NUMBERS 110 medical device
112 analyte sensor
114 insertable portion
116 insertion cannula
118 housing
120 sensor compartment
122 sealed compartment
124 detachable upper cap
126 detachable lower cap
128 intermediate component
130 sealed opening
132 connection portion
134 electronics unit
136 interconnect device
138 flexible printed circuit board
140 protrusion
141 rim
142 electronic component
144 electronic housing
146 lower side
148 adhesive element
150 first portion
152 second portion
154 central portion
156 opening
158 electrical energy reservoir
160 electronic housing
162 loser electronic housing component
164 receptacle
166 upper electronic housing component
168 energy reservoir housing
170 lower energy reservoir housing component
172 receptacle
174 upper energy reservoir housing component
176 skin
178 adhesive surface
180 lower cover
182 upper cover
184 frame

The invention claimed is:

1. An assembly of components for mounting an analyte sensor and an electronics compartment on a user, the assembly comprising:
   a housing defining a sealed sensor compartment, the housing comprising an upper cap, a lower cap, and an intermediate component, the intermediate component being attached to the upper cap and to the lower cap, the housing comprising an electronics compartment comprising an electronics unit;
   a lower cover configured for removal from the assembly prior to analyte sensor insertion;
   an analyte sensor comprising an insertable portion adapted for at least partially being inserted into a user's body tissue;
   a frame displaceable to support the assembly on a user's skin during insertion of the analyte sensor; and
   a cannula attached to the upper cap, the insertable portion of the analyte sensor being received inside the cannula, the intermediate component defining a sealed opening, and the analyte sensor extending from the sealed sensor compartment through the sealed opening to the electronics compartment,
   the analyte sensor being operably connected to the electronics unit,
   the intermediate component defining a cannula aperture extending from an upper surface opening to a lower surface opening,
   the lower cap being configured to seal with the lower surface opening of the intermediate component, the lower cap comprising an interior volume receiving the cannula and the insertable portion of the analyte sensor,
   the upper cap being configured to seal with the upper surface opening of the intermediate component,
   the lower cap being configured for removal prior to insertion of the analyte sensor,
   the upper cap and the cannula being configured for removal from the intermediate component after insertion of the analyte sensor,
   the cannula extending downwardly from the upper cap, through the cannula aperture, and beyond the lower surface opening, the insertable portion of the analyte sensor extending downwardly within the cannula and beyond the lower surface opening, and the lower cap extending downwardly from the intermediate component,
   the housing having a sealed condition, prior to insertion of the analyte sensor, in which the upper cap and the lower cap form with the intermediate component the sealed sensor compartment surrounding and sealing the cannula and the insertable portion of the analyte sensor from an external environment.

2. The assembly of claim 1 in which the lower cover is coupled to the lower cap.

3. The assembly of claim 2 in which the lower cover is configured such that removal of the lower cover removes the lower cap.

4. The assembly of claim 1 in which the assembly comprises:
   in the sealed condition the lower cover is coupled with the lower cap, and the lower cap is sealing the lower surface opening of the intermediate component, and
   in an opened condition, prior to analyte sensor insertion, the lower cover and lower cap are removed from the assembly, and the lower cap is removed from sealing the lower surface opening of the intermediate component.

5. The assembly of claim 4 in which the lower cover, in the sealed condition, comprises a half-shell or a shell surrounding the electronics compartment, the sealed sensor compartment, the cannula, and the analyte sensor.

6. The assembly of claim 1 and further comprising an upper cover configured for removal from the intermediate component after analyte sensor insertion.

7. The assembly of claim 6 in which, in the sealed condition prior to analyte sensor insertion, the lower cover is attached to the upper cover.

8. The assembly of claim 7 in which, in the sealed condition, the lower cover and the upper cover together surround the electronics compartment, the sealed sensor compartment, the upper cap, the lower cap, the cannula, and the analyte sensor.

9. The assembly of claim 7 in which the lower cover is configured to be removed from the upper cover by a rotational movement.

10. The assembly of claim 7 in which the lower cover is configured such that removal of the lower cover from the upper cover removes the lower cap from the intermediate component.

11. The assembly of claim 7 in which, in the sealed condition,
the lower cover is attached to the lower cap, and
the upper cover is directly or indirectly coupled to one or both of the cannula and the upper cap.

12. The assembly of claim 6 in which the upper cover is directly or indirectly coupled to one or both of the cannula and the upper cap.

13. The assembly of claim 12 in which the cannula and upper cap are configured to move from a non-insertion position outside the user's skin to an insertion position with the cannula inserted into the user's body tissue.

14. The assembly of claim 13 in which the electronics compartment is configured to move from a non-contact position outside the user's skin to a contact position on the user's skin.

15. The assembly of claim 14 in which the cannula and upper cap are configured to move from the non-insertion position to the insertion position simultaneous with the electronics compartment moving from the non-contact position to the contact position.

16. The assembly of claim 15 in which the upper cover is coupled with the electronics compartment and moves with the cannula, the upper cap and the electronics compartment.

17. The assembly of claim 1 in which the frame and the upper cover are cylindrical and the frame is received within the upper cover.

18. The assembly of claim 17 in which the frame is received between the upper cover and the electronics compartment.

19. The assembly of claim 18 in which the upper cover, the cannula, the upper cap and the analyte sensor move together relative to the frame from the non-insertion position to the insertion position along with the electronics compartment moving from the non-contact position to the contact position.

20. An analyte monitoring system comprising:
an assembly according to claim 1, the electronics unit comprising an electronic component configured for performing a measurement with the analyte sensor, a device for recording sensor signals, a device for storing measurement signals or measurement data, a transmitter for transmitting sensor signals and/or measurement data, and an energy source; and
a second device, the transmitter transmitting the sensor signals and/or measurement data to the second device.

21. The analyte monitoring system of claim 20 in which the analyte sensor is an electrochemical transcutaneous sensor.

22. The analyte monitoring system of claim 21 in which the electronics unit includes a current source and a voltage measurement device or the electronics unit includes a voltage source and a current measurement device.

23. The analyte monitoring system of claim 22 comprising a continuous glucose monitoring system.

24. A method for mounting an analyte sensor and an electronics compartment on a user using an assembly according to claim 1,
the upper cap, the cannula and the electronics compartment being configured to move together in a direction of insertion to insert the cannula and the insertable portion of the analyte sensor into the user's body tissue, and to mount the electronics compartment on the user's skin,
the method comprising:
removing the lower cap from the assembly;
displacing the frame on the user's skin;
advancing the upper cap, the cannula and the electronics compartment in the direction of insertion to insert the cannula and the insertable portion of the analyte sensor into the user's body tissue, and to mount the electronics compartment on the user's skin,
the upper cap, the cannula, and the electronics compartment advancing in the direction of insertion relative to the frame; and
withdrawing the upper cap and the cannula from the user's body tissue, leaving the analyte sensor inserted into the user's body tissue and the electronics compartment mounted on the user's skin.

25. The method of claim 24 in which the assembly further comprises a lower cover attached to the lower cap.

26. The method of claim 24 in which the assembly further comprises an upper cover directly or indirectly coupled to one or both of the cannula or the upper cap.

27. A mounting assembly for mounting an analyte sensor and an electronics compartment on a user,
the analyte sensor including an insertable portion adapted for at least partially being inserted into a user's body tissue, the analyte sensor being configured to be mounted with the insertable portion extending through the user's skin,
the electronics compartment at least partially receiving an electronics unit operably connected to the analyte sensor, the electronics compartment further comprising an intermediate component comprising an upper surface including an upper surface opening and a lower surface including a lower surface opening, the intermediate component defining a cannula aperture extending from the upper surface opening to the lower surface opening, and the electronics compartment being configured to be mounted on the user's skin,
the mounting assembly comprising:
a frame configured to support the assembly on the user's skin during insertion of the analyte sensor,
a lower cap configured to seal with the lower surface opening of the intermediate component, the lower cap being configured for removal from the intermediate component prior to insertion of the analyte sensor;
an upper cap configured to seal with the upper surface opening of the intermediate component; and
a cannula,
the intermediate component, the lower cap, and the upper cap being configured to form a sealed sensor compartment, the cannula and the insertable portion of the analyte sensor being sealed within the sealed sensor compartment,
the cannula being attached to the upper cap and extending downwardly within the sealed sensor compartment from the upper cap, through the cannula aperture, and beyond the lower surface opening,
the analyte sensor being at least partially received in the cannula and the insertable portion of the analyte sensor extending downwardly within the cannula through the cannula aperture and beyond the lower surface opening, and
the lower cap extending downwardly from the lower surface of the intermediate component and comprising an interior volume receiving the cannula and the insertable portion of the analyte sensor, the sealed sensor compartment being connected to the electronics compartment via a sealed opening, the analyte sensor extending through the sea led opening from the sea led sensor compartment to the electronics compartment, and the upper cap and cannula being configured for removal from the intermediate component after insertion of the analyte sensor.

* * * * *